US010953110B2

(12) United States Patent
Zheng et al.

(10) Patent No.: US 10,953,110 B2
(45) Date of Patent: Mar. 23, 2021

(54) DUAL EMISSIVE METAL NANOPARTICLES AS RATIOMETRIC PH INDICATORS

(71) Applicant: The Board of Regents of The University of Texas System, Austin, TX (US)

(72) Inventors: Jie Zheng, Allen, TX (US); Jinbin Liu, Plano, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 867 days.

(21) Appl. No.: 14/697,200

(22) Filed: Apr. 27, 2015

(65) Prior Publication Data
US 2015/0306253 A1 Oct. 29, 2015

Related U.S. Application Data

(60) Provisional application No. 61/984,456, filed on Apr. 25, 2014.

(51) Int. Cl.
A61K 49/00 (2006.01)
(52) U.S. Cl.
CPC ................. A61K 49/0065 (2013.01)
(58) Field of Classification Search
CPC ............ A61K 49/0052; A61K 49/0065; A61K 49/0093
See application file for complete search history.

(56) References Cited

U.S. PATENT DOCUMENTS

| | | |
|---|---|---|
| 2005/0118252 A1 | 6/2005 | Bae et al. |
| 2005/0277739 A1 | 12/2005 | Yang et al. |
| 2009/0068505 A1 | 3/2009 | Adzic et al. |
| 2009/0226376 A1 | 9/2009 | Grimmond et al. |
| 2010/0075339 A1 | 3/2010 | Rector et al. |
| 2010/0255311 A1 | 10/2010 | Lee et al. |
| 2010/0260686 A1 | 10/2010 | Zhang et al. |
| 2011/0105437 A1 | 5/2011 | Ralph et al. |
| 2011/0111518 A1 | 5/2011 | Zheng et al. |
| 2013/0039848 A1 | 2/2013 | Bradbury et al. |
| 2013/0183665 A1 | 7/2013 | Chan et al. |

FOREIGN PATENT DOCUMENTS

| | | |
|---|---|---|
| WO | WO 2012/039685 | 3/2012 |
| WO | WO 2012/037667 | 3/2013 |
| WO | WO 2012/104831 | 8/2013 |

OTHER PUBLICATIONS

Luo et al., JACS, 2012, 134, p. 16662-70.*
Yamada et al., J. Phys. Chem. C, 2007, 111, p. 11246-11251 (Year: 2007).*
Marin et al., Angew. Chem. Int. Ed., 2012, 51, p. 9657-9661. (Year: 2012).*
Yang et al., Journal of Biomedical Nanotechnology, 2013, vol. 9, p. 1827-1836. (Year: 2013).*
Briggs, et al., "A pH sensitive fluorescent cyanine dye for biological applications", *Chem. Commun..* 2323-2334, 2000.
Brinas, et al., "Gold nanoparticle size controlled by polymeric Au(I) thiolate precursor size", *Journal of the American Chemical Society*, 130:975-982, 2008.
Casals, et al, "Time evolution of the nanoparticle protein corona", *ACS Nano*, 4:3623-3632, 2010.
Choi, et al., et al., "Renal clearance of quantum dots", *Nature Biotechnology*, 25:1165-1170, 2007.
Dennis, et al., "Quantum dot-fluorescent protein FRET probes for sensing intracellular pH", *ACS Nano* 6:2917-2924, 2012.
Glaasker, et al., "The application of pH-sensitive fluorescent dyes in lactic acid bacteria reveals distinct extrusion systems for unmodified and conjugated dyes", *Molecular Membrane Biology*, 13:173-181, 1996.
Jin and Gao, "Plasmonic fluorescent quantum dots," *Nat. Nanotechnol.*, 4:571-576, 2009.
Liu et al., "PEGylation and zwitterionization: pros and cons in renal clearance and tumor targeting of near-IR-emitting gold nanoparticles," *Angew. Chem., Int. Ed.*, 52:12572-12576, 2013.
Liu et al., "Potential health impact on mice after nasal instillation of nano-sized copper particles and their translocation in mice," *J Nanosci. Nanotechnol.*, 9:335-6343, 2009.
Liu et al., "Renal clearable inorganic nanoparticles: a new frontier of bionanotechnology," *Mater. Today*, 16:477-486, 2013.
Liu, et al., "Compact biocompatible quantum dots functionalized for cellular imaging", *Journal of the American Chemical Society*, 130:1274-1284, 2008.
Liu, et al., "pH-sensitive photoluminescence of CdSe/ZnSe/ZnS quantum dots in human ovarian cancer cells", *The Journal of Physical Chemistry C, Nanomaterials and Interfaces*, 111:2872-2878, 2007.
PCT International Preliminary Report on Patentability, issued in International Application No. PCT/US2012/042525, dated Dec. 17, 2012.
PCT International Search Report and Written Opinion, issued in International Application No. PCT/US2014/055801, dated Jan. 26, 2015.
PCT International Search Report, issued in International Application No. PCT/US2012/042525, dated Sep. 13, 2012.
Povrozin, et al., "Near-infrared, dual-ratiometric fluorescent label for measurement of pH", *Analytical Biochemistry* 390:136-140, 2009.
Shtyrlin et al., "Structure, stability, and ligand exchange of copper(II) complexes with oxidized glutathione," *J. Inorg. Biochem.*, 99:1335-1346, 2005.
Snee, et al., "A ratiometric CdSe/ZnS nanocrystal pH sensor", *Journal of the American Chemical Society* 128:13320-13321, 2006.
Urano, et al., "Selective molecular imaging of viable cancer cells with pH-activatable fluorescnence probes", *Nature Medicine*, 15:104-109, 2009.

(Continued)

*Primary Examiner* — Michael G. Hartley
*Assistant Examiner* — Leah H Schlientz
(74) *Attorney, Agent, or Firm* — Parker Highlander PLLC

(57) ABSTRACT

In some aspects, the present disclosure provides a dual emissive pH response noble metal nanoparticle which produces a ratiometric fluorescence signal based upon changes in the pH. In another aspect, the noble metal nanoparticle may be used in bioimaging applications as well as to detect in vivo changes of pH.

20 Claims, 13 Drawing Sheets

(56) References Cited

OTHER PUBLICATIONS

Wang, et al., "Near-IR luminescence of monolayer-protected metal clusters", *Journal of the American Chemical Society*, 127:812-813, 2005.
Zheng, et al., "Highly fluorescent noble-metal quantum dots", *Annual Review of Physical Chemistry*, 58:409-431, 2007.

* cited by examiner

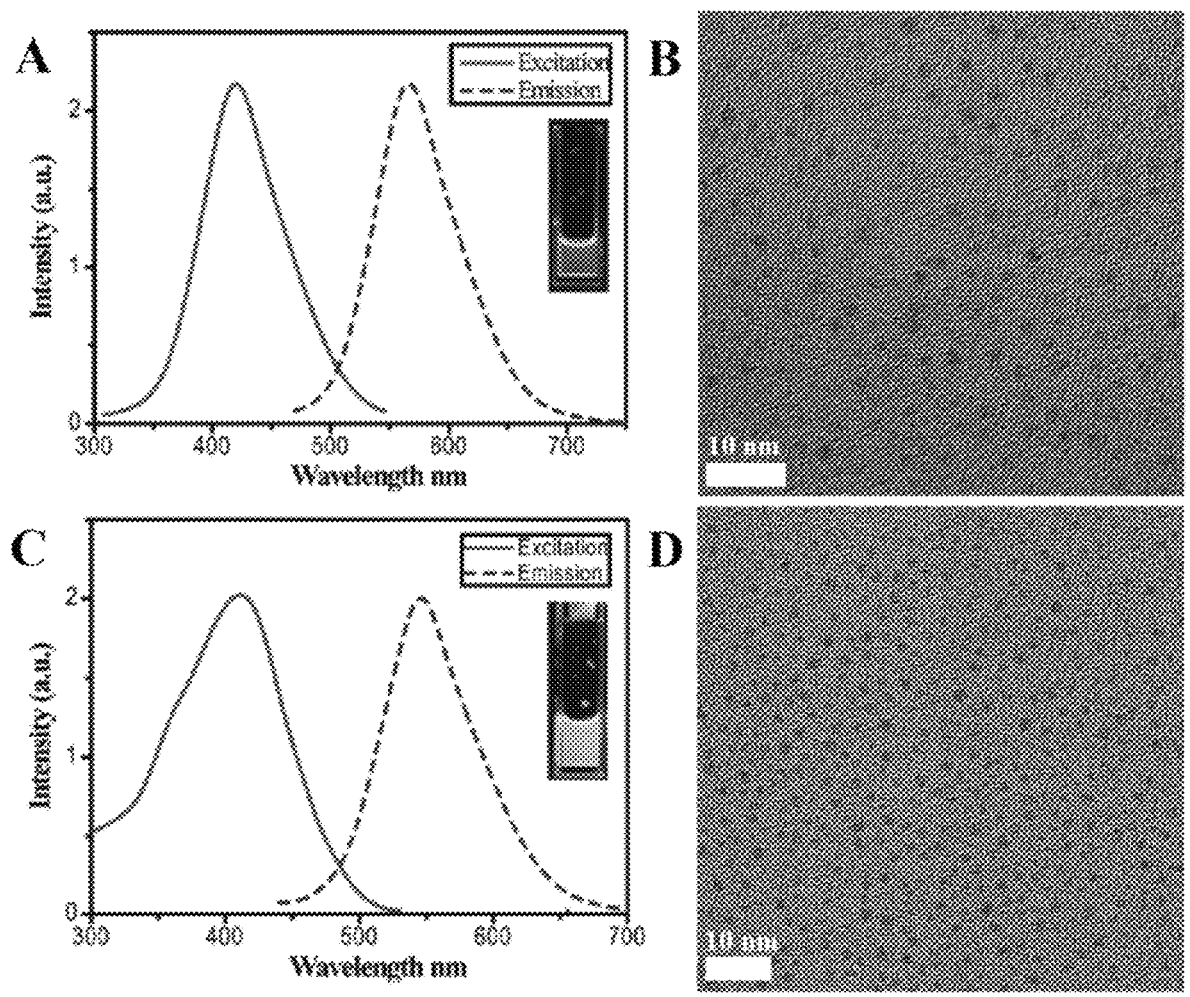
FIG. 1A-D

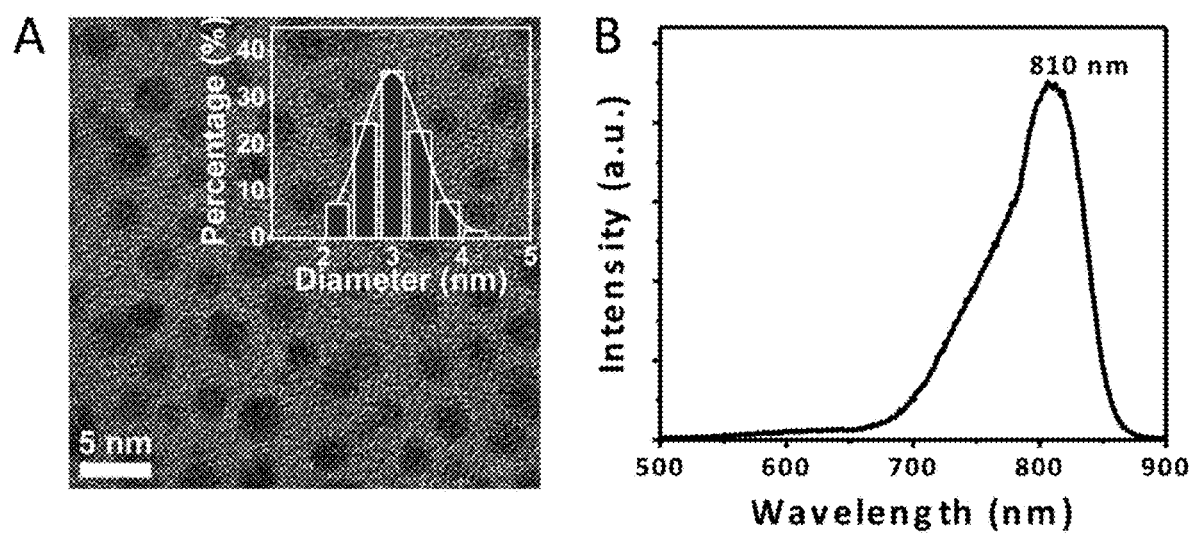
FIGS. 2A-B

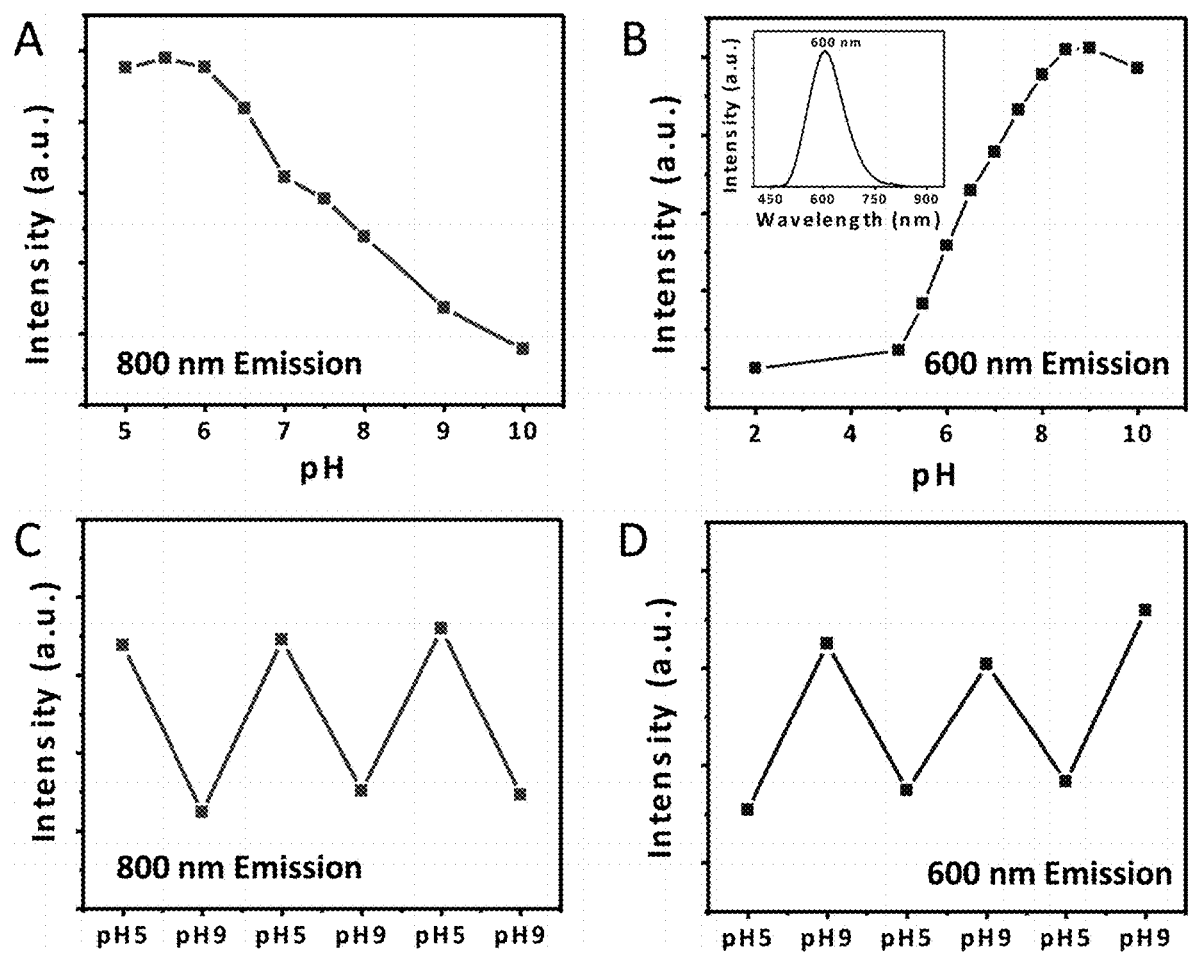
FIGS. 3A-D

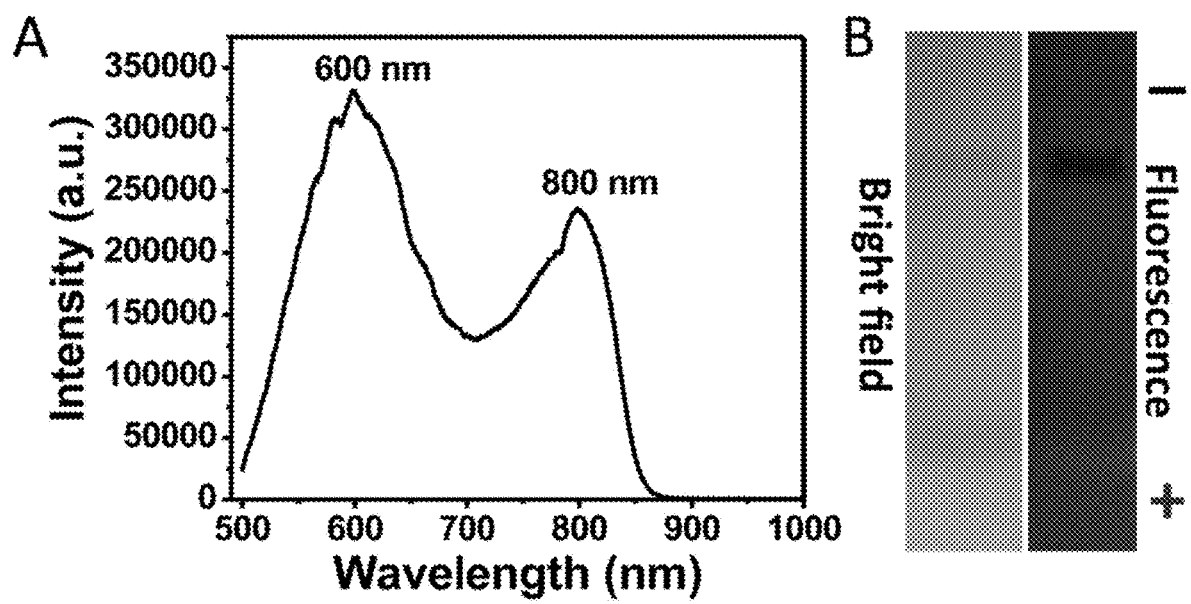
FIGS. 4A-B
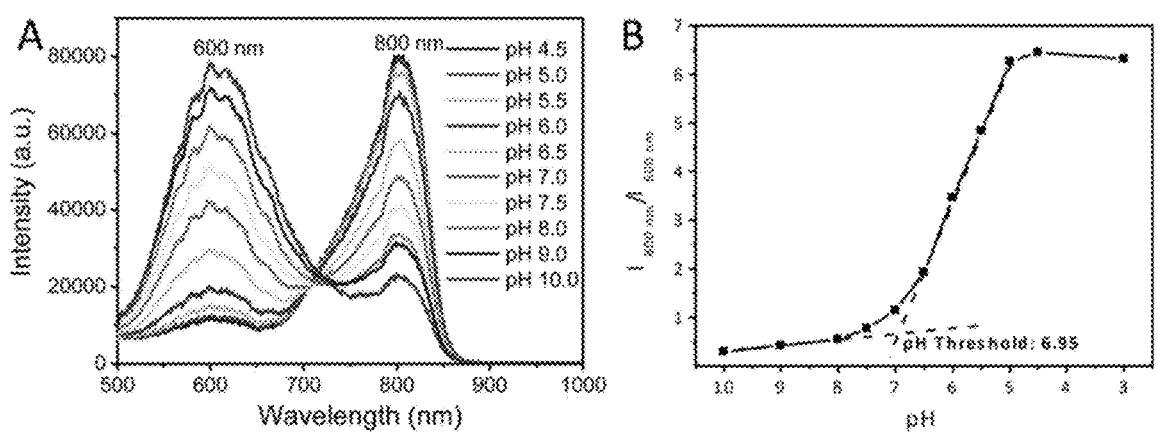
FIGS. 5A-B

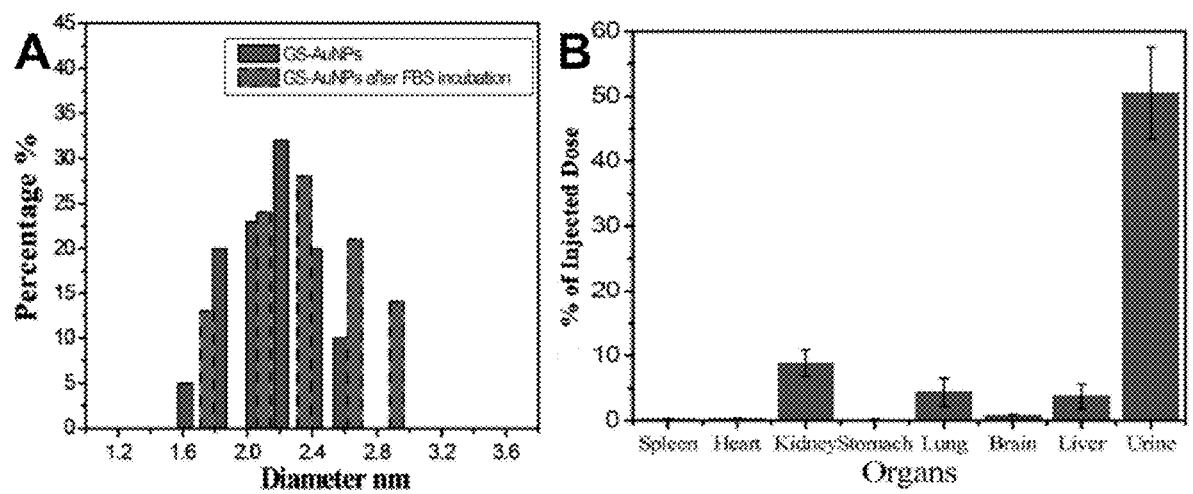
FIGS. 6A-B
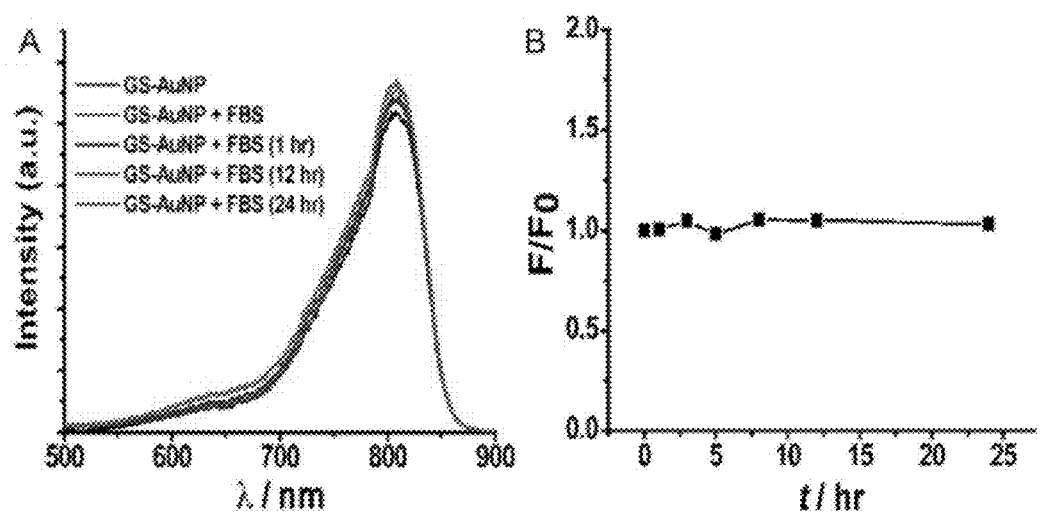
FIGS. 7A-B

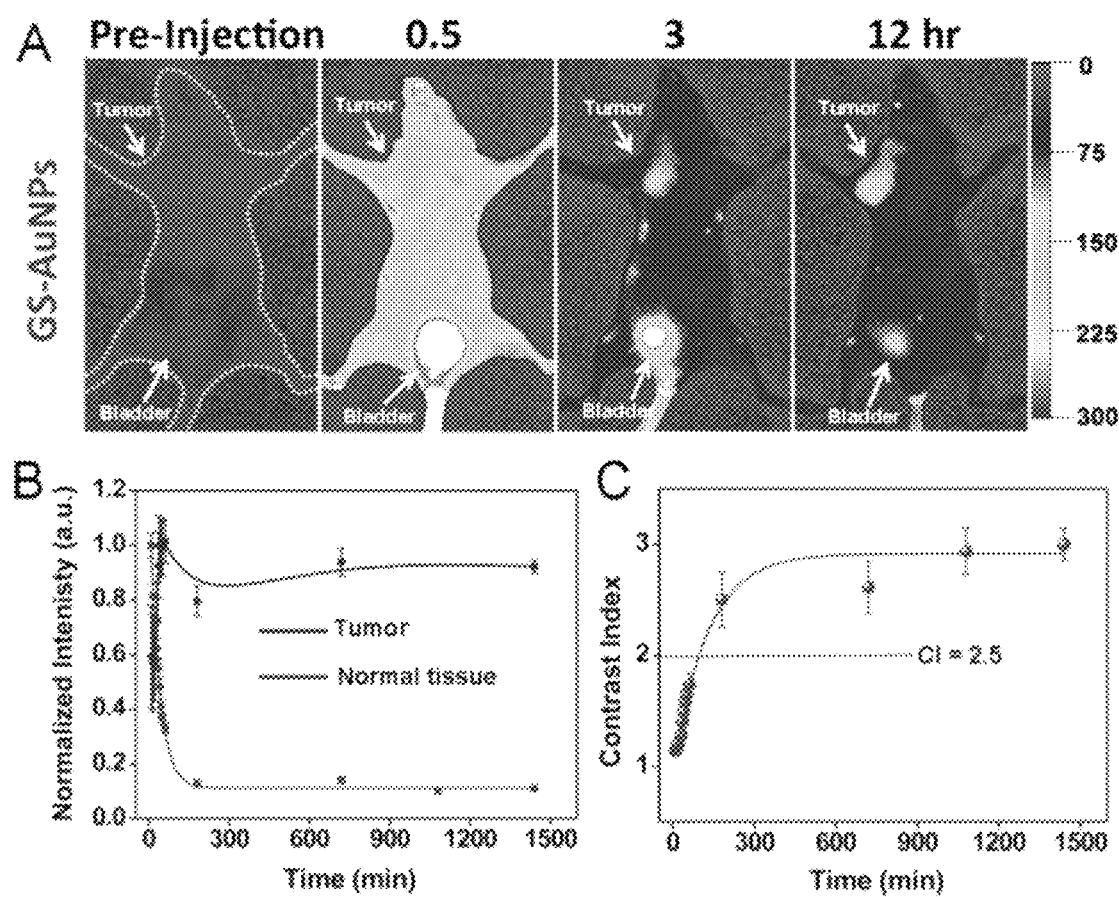
FIGS. 8A-C

DUAL EMISSIVE METAL NANOPARTICLES AS RATIOMETRIC PH INDICATORS

CROSS-REFERENCE TO RELATED APPLICATIONS

This application claims the benefit of U.S. Provisional Patent Application No. 61/984,456, filed Apr. 25, 2014, the entirety of which is incorporated herein by reference.

STATEMENT REGARDING FEDERALLY-SPONSORED RESEARCH OR DEVELOPMENT

This invention was made with government support under Grant No. R21EB009853 awarded by the National Institutes of Health. The government has certain rights in the invention.

BACKGROUND OF THE INVENTION

1. Field of the Invention

The present disclosure generally relates to the fields of nanoparticles and pH probes. More specifically, it relates to the use of nanoparticles to image and detect pH changes around tissues.

2. Related Art

Among many tools used for pH imaging (Hashim, et al., 2011; Khramtsov, 2005; Gillies, 2004), fluorescence imaging techniques are particularly attractive because of their low-running cost, high sensitivity and high tempospatial resolutions (Schaeferling, 2012; Sevick-Muraca, 2012; Ardeshirpour, et al., 2011; Mansfield, 2010). To make fluorescence-imaging techniques sensitive enough to detect slight changes in pH, a large number of fluorescent pH indicators have been developed to enhance imaging contrasts (Han and Burgess, 2010; Bizzarri, et al., 2009; Chudakov, et al., 2005). Furthermore, fluorescence-imaging effects such as photon-induced electron transfer (PET) effect, Förster resonance energy transfer (FRET) effect, as well as self-quenching can be used to develop pH fluorescence-imaging techniques using dyes.

The strengths of luminescent inorganic nanoparticles (NPs) in emission robustness and brightness have driven significant efforts to develop inorganic NP based fluorescent pH indicators (Dennis, et al., 2012; Liu, et al., 2008). For instance, quantum dots (QDs) made of CdSe/ZnSe/ZnS nanocrystals exhibit pH-dependent emission once they are coated with mercaptoacetic acids (MAAs), and fluorescence intensity can be increased more than 5 times with increasing pH from 4 to 10 (Liu, et al., 2007). The observed pH-dependent emission originated from the dissociation of MAA ligands from ZnS surface, resulting in the decrease of quantum efficiency of QDs in the acidic environment (Liu, et al., 2007). However, the limitation of such pH responsive QDs is that their pH response is irreversible and emission becomes weaker in the acidic environment. To address this challenge, Bawendi et al. conjugated a pH sensitive squaraine dye (energy acceptor) to the surface of 3 nm ZnS/CdSe nanocrystal (energy donor), and observed that pH-dependent FRET between CdSe and squaraine dye (Snee, et al., 2006). Under basic conditions (pH 10), energy transfer from the QDs to the dye was inefficient; as a result, the emission was dominated by QDs' emission at 613 nm. However, once pH was lowered to 6, FRET from the QDs to the dye becomes much more efficient, and the emission from the dye at 650 nm became dominated. The ratio of emission from QDs to that from dye can be used to quantify the pH in the local environment. Not limited to pH sensitive organic dyes, Bao et al. recently demonstrated that QDs can also be conjugated with pH sensitive fluorescence proteins and such FRET-based QD-FP exhibits more than a 12-fold change in FP/QD emission ratio once the pH is changed from pH 6 to pH 8, making it feasible to track pH temporally and spatially in a living cell (Dennis, et al., 2012).

However, the delivery of fluorescent pH indicators into in vivo imaging of acidic tumor microenvironment has been severely blocked because of several key issues. First, the pharmacokinetics of small organic dye based pH indicators is not suitable for long-term tumor imaging. Because small molecules are rapidly cleared out of the body within minutes, tumor targeting efficiency of small dye molecules usually extremely low and the retention time of the dye molecules in the tumor is also very short (Matsumura and Maeda, 1986; Hirsjarvi, et al., 2011), precluding them from long-term quantitative imaging of extracellular pH ($pH_e$) of tumor microenvironment. Furthermore, nonspecific serum protein adsorption makes pH responsive nanoprobes less sensitive to external acidic microenvironment. Because of large surface/volume ratio and high surface potential, serum proteins in the blood tend to be nonspecifically adsorbed onto probes and form protein coronas (buffering layers) on the probe surface, which make the probe emission much less sensitive to external pH environment (Lundqvist, et al., 2008; Casals, et al, 2010; Lesniak, et al., 2010; Gao, et al., 2002). Additionally, severe nonspecific accumulation of fluorescent nanoprobes in reticuloendothelial system (RES) organs results in low tumor targeting efficiency and potential long-term nanotoxicity. Most of pH-responsive fluorescent nanoprobes such as polymer NPs loaded with fluorescent dyes or QDs coated with fluorescent dyes have hydrodynamic diameters (HD) above 10 nm, much larger than the cutoff size (5 nm) for kidney filtration; as a result, they are not renal clearable and the majority of the probes are often rapidly sequestered by RES organs, leading to very low targeting efficiency and potential long-term nanotoxicity (Choi, et al., 2007) For example, nearly 90% of non-PEGylated QDs with size ranging from 12-21 nm found in RES organs were actually eliminated from the bloodstream within 2 min, making it difficult to deliver significant amount of particles to disease sites (Schipper, et al., 2009). Rapid internalization of indicators into the lysosomes makes it difficult to accurately quantify extracellular $pH_e$ of tumor microenvironment. Indicators conjugated with active targeting ligands or serum proteins often initiate rapid receptor-mediated endocytosis of the tumor cells (Canton and Battaglia, 2012); as a result, pH values reported by the indicators reflect acidic environment of endosomes (pH: ~5.5) or lysosomes (pH: ~4.5) (Lakadamyali, et al., 2006) rather than extracellular $pH_e$ (pH: ~6.8) of tumor microenvironment. For instance, BODIPY or Av-TM-Q7 based fluorescent pH indicators described above are actually activated in the lysosome rather than in acidic microenvironment (Urano, et al., 2009) or lack of ratiometric pH indicators with dual color emission in near-infrared (NIR) range limits their in vivo imaging applications. Because of the limited penetration depth of the light and strong blue-green autofluorescence range from animal tissues, NIR emitting indicators will be highly desired. While several NIR emitting organic dyes have been used to design pH responsive fluorescent indicators (Glaasker, et al., 1996; Briggs, et al., 2000; Mishra, et al., 2000; Povrozin, et al., 2009), very few of them can give ratiometric dual-color emissions in both red and NIR range, limiting their applications in real-time imaging of native acidic tumor microenvironment.

SUMMARY OF THE INVENTION

In one aspect, the present disclosure provides a nanoparticle comprising a noble metal nanoparticle, wherein: the surface of the noble metal nanoparticle is coated with a first pH-dependent ligand; and the noble metal nanoparticle is about 0.1 nm to about 5 nm in diameter and comprises a mixture of metal atoms in the ground oxidation state and a charged oxidation state. In some embodiments, the mixture of metal atoms in the ground oxidation state and the charged oxidation state produce an interband emission when exposed to an excitation source. In some embodiments, the excitation source exposes the nanoparticle to light of a wavelength from about 450 nm to about 600 nm. In some embodiments, the wavelength is about 500 nm to about 680 nm. In some embodiments, the first pH-dependent ligand and the metal atoms in the noble metal nanoparticle interact to produce a surface-state emission when exposed to an excitation source. In some embodiments, the excitation source exposes the nanoparticle to light of a wavelength from about 450 nm to about 600 nm. In some embodiments, the wavelength is about 700 nm to about 1200 nm. In some embodiments, the noble metal nanoparticle is a gold nanoparticle. In other embodiments, the noble metal nanoparticle is a silver nanoparticle. In some embodiments, the charged oxidation state is the +1 oxidation state. In some embodiments, the first pH-dependent ligand is a mercapto containing alkane$_{(C\leq12)}$ or substituted alkane$_{(C\leq12)}$, amino acid, amino acid derivative, 2 to 10 amino acid long peptide, or protected amino acid. In some embodiments, the first pH-dependent ligand is 2-mercaptoethanol, cysteamine, 3-mercaptopropionic acid, N-acetyl-L-cysteine, (2-mercaptopropionyl)glycine and glutathione. In some embodiments, the first pH-dependent ligand is glutathione. In some embodiments, the coating further comprises a second pH-dependent ligand. In some embodiments, the second pH-dependent ligand is a mercapto containing alkane$_{(C\leq12)}$ or substituted alkane$_{(C\leq12)}$, amino acid, amino acid derivative, 2 to 10 amino acid long peptide, or protected amino acid. In some embodiments, the second pH-dependent ligand is 2-mercaptoethanol, cysteamine, 3-mercaptopropionic acid, N-acetyl-L-cysteine, and (2-mercaptopropionyl)glycine. In some embodiments, the ratio of the first and second pH-dependent ligand to the metal atoms in the noble metal nanoparticle is from about 3:1 to about 1:3. In some embodiments, the ratio is about 1:1. In some embodiments, the noble metal nanoparticle is about 1.5 nm to about 3 nm in diameter. In some embodiments, the noble metal nanoparticle is about 1.7 nm to about 2.3 nm in diameter. In some embodiments, the nanoparticle further comprises a hydrodynamic ratio of the noble metal nanoparticle is from about 2.5 nm to about 6 nm. In some embodiments, the hydrodynamic ratio of the noble metal nanoparticle is from about 3.0 nm to about 4.0 nm. In some embodiments, the interband emission and the surface-state emission results in a fluorescence emission spectra which contains a first fluorescence peak for the interband emission and a second fluorescence peak for the surface-state emission. In some embodiments, the first and second fluorescence peaks are centered in the red and near-infrared range. In some embodiments, the first fluorescence peak is centered from about 500 nm to about 1200 nm. In some embodiments, the first fluorescence peak is centered from about 500 nm to about 750 nm. In some embodiments, the first fluorescence peak is centered about 600 nm. In some embodiments, the first fluorescence peak is centered about 680 nm. In some embodiments, the second fluorescence peak is centered from about 750 nm to about 1200 nm. In some embodiments, the second fluorescence peak is centered about 800 nm. In some embodiments, the second fluorescence peak is centered about 920 nm to about 1100 nm. In some embodiments, interband or surface-state emission of the nanoparticle change based upon the pH of the environment. In some embodiments, a ratio of the peak area from the first and second fluorescence peak changes as the pH of the environment changes. In some embodiments, the noble metal nanoparticle comprises a pH threshold for observed pH-dependent emission is from about 6.5 to about 7.5. In some embodiments, the pH threshold for observed pH-dependent emission is about 6.95. In some embodiments, the noble metal nanoparticle further comprises a targeting ligand. In some embodiments, the targeting ligand is a small molecule, protein, antibody, or antibody fragment which causes the nanoparticle to accumulate at a given point. In some embodiments, the noble metal nanoparticle further comprises a pH dependent membrane adsorption mechanism. In some embodiments, the pH dependent membrane absorption mechanism comprises coating the surface of the noble metal nanoparticle with a mixture of glutathione and cysteamine. In some embodiments, the mixture of glutathione and cysteamine comprises a ratio of glutathione to cysteamine from about 6 glutathione per cysteamine to about 6 cysteamine per glutathione. In some embodiments, the ratio of glutathione to cysteamine is selected from about 4:1, 2:1, 3:2, 1:1, 2:3, 1:2, 2:5, and 1:3.

In another aspect, the present disclosure provides a method of using a noble metal nanoparticle coated with a pH dependent ligand described herein to image a tumor comprising: contacting the noble metal nanoparticle with the extracellular matrix around the tumor; exposing the nanoparticle to an excitation source; and obtaining a fluorescence reading from a first and second fluorescence emission wavelength selected from an interband and surface-state fluorescence emission of the nanoparticle. In some embodiments, the excitation source produces light of a wavelength from about 450 nm to about 600 nm. In some embodiments, the wavelength is about 600 nm to about 800 nm. In some embodiments, the first fluorescence emission wavelength is from about 500 nm to about 750 nm. In some embodiments, the first fluorescence emission wavelength is about 600 nm. In some embodiments, the first fluorescence emission wavelength is about 680 nm. In some embodiments, the second fluorescence emission wavelength is from about 750 nm to about 1200 nm. In some embodiments, the second fluorescence emission wavelength is 800 nm. In some embodiments, the extracellular matrix further comprises an extracellular pH (pH$_e$) which is different from the pH of normal tissue. In some embodiments, the pH$_e$ is from about 6 to about 7.4. In some embodiments, the pH$_e$ is from about 6.2 to about 6.9. In some embodiments, the pH$_e$ is about 6.8. In some embodiments, the noble metal nanoparticle is a gold nanoparticle. In other embodiments, the noble metal nanoparticle is a silver nanoparticle. In some embodiments, the noble metal nanoparticle shows little nonspecific absorption of serum proteins. In some embodiments, the noble metal nanoparticles show little change in the emission properties in physiological conditions and in the presence on serum proteins. In some embodiments, the method further comprises measuring the emission of the noble metal nanoparticles at 600 and 800 nm and calculating the ratio of the emission at 800 nm around the tumor to the emission at 600 nm around the tumor. In some embodiments, the ratio of the emission at 800 nm to the emission around at 600 nm is compared to the ratio of the emission at 800 nm in the bladder to the emission at 600 nm in the bladder to obtain the pH around the tumor. In some embodiments, the ratio of the emission at 800 nm in the bladder to the emission at 600 nm in the bladder is correlated with the pH of the urine to obtain a pH value for a given ratio of the emission at 800 nm to the emission at 600 nm. In some embodiments, the pH dependent ligand coating on the noble metal nanoparticle further comprises a first and a second pH dependent ligand. In some embodiments, the first pH dependent ligand is a mercapto containing alkane$_{(C\leq12)}$ or substituted alkane$_{(C\leq12)}$, amino acid, amino acid derivative, 2 to 10 amino acid long peptide, or protected amino acid. In some embodiments, the first pH dependent ligand is 2-mercaptoethanol, cysteamine, glutathione, 3-mercaptopropionic acid, N-acetyl-L-cysteine, and (2-mercaptopropionyl)glycine. In some embodiments, the second pH dependent ligand is a mercapto containing alkane$_{(C\leq12)}$ or substituted alkane$_{(C\leq12)}$, amino acid, amino acid derivative, 2 to 10 amino acid long peptide, or protected amino acid. In some embodiments, the second pH dependent ligand is 2-mercaptoethanol, cysteamine, glutathione, 3-mercaptopropionic acid, N-acetyl-L-cysteine, and (2-mercaptopropionyl)glycine. In some embodiments, the noble metal nanoparticle further comprises a pH dependent adsorption mechanism. In some embodiments, the pH dependent absorption mechanism comprises adding a glutathione as the first pH dependent ligand and cysteamine as the second pH dependent ligand. In some embodiments, the ratio of the first pH dependent ligand to the second pH dependent ligand is from about 6:1 to about 1:6. In some embodiments, the ratio of the first pH dependent ligand to the second pH dependent ligand is selected from about 4:1, 2:1, 3:2, 1:1, 2:3, 1:2, and 1:4. In some embodiments, the noble metal nanoparticle exhibits significant renal clearance. In some embodiments, the renal clearance is greater than 50% excreted by urine within 24 hours. In some embodiments, the noble metal nanoparticle shows less than 10% accumulation in the liver. In some embodiments, the tumor is imaged in vivo.

In yet another aspect, the present disclosure provides a method of imaging a change in a patient's extracellular physiological pH in vivo comprising administering to the patient a noble metal nanoparticle coated with one or more pH responsive ligands with two or more emission wavelengths described herein.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made within the scope of the disclosure without departing from the spirit thereof, and the disclosure includes all such substitutions, modifications, additions and/or rearrangements.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-1D show the characterization of glutathione coated luminescent AuNPs. FIG. 1A shows the excitation and emission spectra of OGS-AuNPs in aqueous solution and contains a picture of OGS-AuNPs taken with excitation of a handheld long-wave UV lamp (365 nm). FIG. 1B shows a typical TEM image of OGS-AuNPs (scale bar: 10 nm). FIG. 1C shows the excitation and emission spectra of YGS-AuNPs in aqueous solution and contains a picture of YGS-AuNPs taken with excitation of a hand-held long-wave UV lamp (365 nm). FIG. 1D shows a typical TEM image of YGS-AuNPs (scale bar: 10 nm).

FIGS. 2A-B show the size (FIG. 2A) and emission spectrum (FIG. 2B) of IR-emitting glutathione coated AuNPs. Scale bar: 5 nm, which can be excitation from 400 nm to 560 nm.

FIGS. 3A-3D show the pH-dependent emissions of 800 nm emitting AuNPs (FIG. 3A) and 600 nm emitting AuNPs (FIG. 3B). Additionally, emission reversibility studies of 800 nm emitting AuNPs (FIG. 3C) and 600 nm emitting AuNPs (FIG. 3D) at pH 5 and pH 9 are shown.

FIGS. 4A-B show (FIG. 4A) dual-emissive AuNPs emitting at 600 nm and 800 nm. (FIG. 4B) Gel electrophoresis shows that emission from a single species (lower band). The grey band in the bright field was the loading well.

FIGS. 5A-B show (FIG. 5A) luminescence spectra of 800/600 dual-emissive AuNPs at the different pHs (FIG. 5B). The relationship between intensity ratio of 800 nm emission to 600 nm in a pH range from 10 to 3. The pH threshold for the observed pH-dependent emission is around 6.95.

FIGS. 6A-B show (FIG. 6A) GS-AuNPs size distribution by number in PBS with (light gray) and without (dark gray) incubation with FBS. (FIG. 6B) Biodistribution of GS-AuNPs in mice (n=3) 24 h after intravenous (iv) injection. The percentage of injected dose (ID) was calculated based on the gold concentration measured by ICP-MS.

FIGS. 7A-B show stability studies of GS-AuNP over a 24 h incubation at 37° C. in PBS solution supplemented with 10% FBS. (FIG. 7A) The fluorescence spectra of the GS-AuNPs after incubation with FBS at 0, 1, 12 and 24 h; (FIG. 7B) The time-dependence of the ratio between the fluorescence intensity (F) at different incubation time and the fluorescence intensity of GS-AuNPs right after incubated with FBS ($F_0$).

FIGS. 8A-8C show passive tumor targeting of 800 nm emitting GS-AuNPs. (FIG. 8A) Representative in vivo NIR fluorescence images of MCF-7 tumor-bearing mice iv injected with GS-AuNPs at p.i. time points of 0.5, 3, and 12 h, respectively. (FIG. 8B) Retention kinetics of the probes in normal tissue and tumor showing EPR effect in ultrasmall GS-AuNPs. (FIG. 8C) Contrast index (CI) of GS-AuNPs at different p.i. time points showing that the particles reach CI threshold (CI=2.5 considered as high S/N ratio) after ~3 h.

(FIG. 11A) TEM image and luminescence image of the AuNPs are shown. (FIG. 11B) The core size of the nanoparticles is 2.7±0.5 nm, and the nanoparticles have a hydrodynamic diameter (HD) of 3.1±0.4 nm in aqueous solution.

(FIG. 12D) Colocalization of GC-AuNPs with membrane dye DiR on live cell membrane (scale bar, 20 μm).

DETAILED DESCRIPTION OF THE DISCLOSURE

Figure 9:
FIG. 9 shows fluorescence image of a mouse i.v. injected with 600 nm emitting AuNPs.
Figure 10:
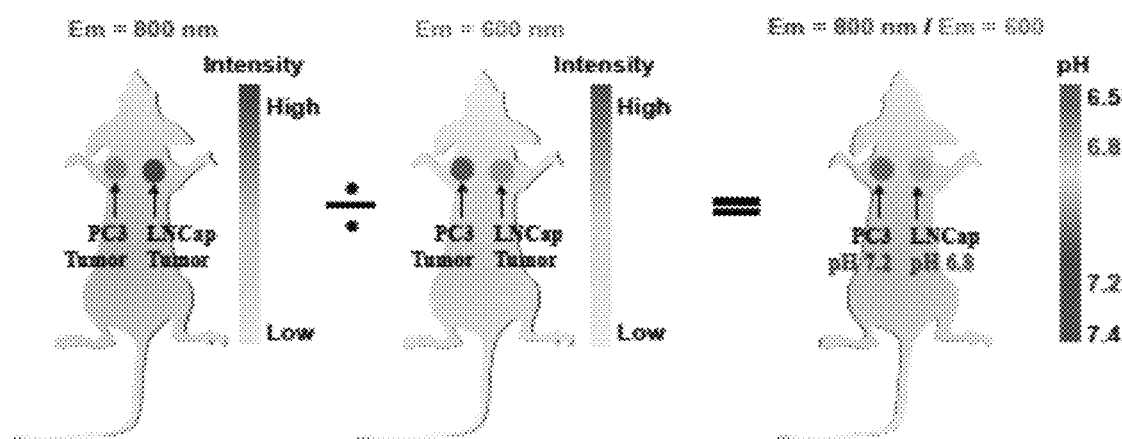
FIG. 10 shows a simple scheme showing the proposed ratio imaging that not only offers quantitative $pH_e$ of acidic tumor but also allows imaging of acidic tumors at a high spatial resolution.

Acidosis, induced by glycolysis under hypoxic conditions, is a universal feature of solid tumors where extracellular pH ($pH_e$) of tumor microenvironment is slightly lower than that of normal tissues (pH 7.4) with a range from pH 6.2-6.9 (Brown, 2002). This tiny pH differences in extracellular microenvironment induce degradation of vital biochemical processes and death of the normal cells and initiate tumor progression and metastasis (Gatenby and Gawlinksi, 1996; Gatenby, et al., 2006, arrive at the features. Therefore, real-time imaging of $pH_e$ of tumor microenvironment at high temporal and spatial resolution is extreme importance of fundamental understanding of cancer biology and early cancer diagnosis but remains highly challenging because very few pH indicators can carry out this task at the in vivo level.

Luminescent AuNPs are a class of new gold nanostructures, which can give intrinsic and tunable emission with no need of conjugation of additional fluorophores (Zheng, et al., 2012; Zheng, et al., 2004; Zheng, et al., 2007; Shang, et al., 2011). Research has shown that luminescence from AuNPs can be tuned from blue to NIR by changing particle size, valence state, surface ligands and crystallite size (Zhou, et al., 2012). The present disclosure relates to renal clearable luminescent AuNPs with dual-color emissions that response to physiological pH changes in opposite ways, so that ratio of these two emissions can be used for quantitative imaging of acidic tumor microenvironment in real time without inducing nonspecific protein adsorption and severe accumulation in RES organs. By further incorporating pH-dependent membrane adsorption into these luminescent nanoparticles based ratiometric pH indicators, the present disclosure uses the synergic pH-dependent responses to further enhance acidic tumor target and obtain more accurate and quantitative imaging of extracellular acidic microenvironment.

The present disclosure relates to ratiometric pH indicators based upon noble metal nanoparticles which present dual emision spectra which have opposite response to pH, have emission in the red or near infared spectra, are retained near the tumor for long enough to obtain suitable imaging while not being internalized, target acidic tumors with little accumulation in RES organs. These nanoparticles will be useful in advancing the understanding of tumor microenvironments and provide a greater ability to image the acidic microenvironment of the tumor at a higher spatial resolution.

I. NANOPARTICLES

The disclosure provides nanoparticle compositions comprising a nanoparticle, methods for preparing the nanoparticle compositions and methods of using the nanoparticle compositions. The compositions of the disclosure comprise noble metal nanoparticles, which are capable of emitting in the near-infrared region of the light spectrum. In some embodiment, the noble metal nanoparticle comprises between 2 and 1000 noble metal atoms. The noble metals that may be used are selected from the group consisting of gold, silver, and copper. The properties of the nanoparticles enable excretion through the kidneys, as well as selective uptake and retention in tumors compared with normal tissues. This, along with the lack of in vivo toxicity, has resulted in a composition that is promising for translation to the clinic. In some embodiment, the nanoparticle may comprise up to three distinct photophysical mechanisms including sp-sp intraband, sp-d interband, and surface-state emission. In some embodiments of the present disclosure, the nanoparticles comprise two distinct emission mechanisms. In some embodiments, those emission mechanisms are interband emission and surface-state emission.

In some aspects, the nanoparticles composition excites at a wavelength from about 450 nm to about 680 nm, such as from about 450 nm to about 600 nm, from about 500 nm to about 680 nm, or from about 450, 460, 470, 480, 490, 500, 510, 520, 530, 540, 550, 560, 570, 580, 590, 600, 610, 620, 630, 640, 650, 660, 670, to about 680 nm, or any range derivable thereof. In other aspects, the nanoparticle composition excites at a wavelength from about 600 nm to about 800 nm, such as from about 600, 610, 620, 630, 640, 650, 660, 670, 680, 690, 700, 710, 720, 730, 740, 750, 760, 770, 780, 790, to about 800 nm, or any range derivable thereof. As described above, the nanoparticles compositions which may be used emit photons at a wavelength from about 500 nm to about 1200 nm such as from about 500 nm to about 750 nm, from about 750 nm to about 1200 nm, from about 900 nm to 1200 nm, or from about 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, to about 1200, or any range derivable thereof. In some embodiments, the nanoparticle composition emits photons in the near-infrared range such as from 750 nm to about 1100 nm.

In some aspects, the nanoparticles of the present disclosure relate to producing a ratiometric response to cellular and extracellular pH. In some particular embodiments, the nanoparticles may comprise one or more surface ligand which contains a pH responsive element. In some embodiments, these surface ligands contain thiol groups such 2-mercaptoethanol, 3-mercaptopropionic acid, or N-acetyl-L-cysteine, as well as glutathione.

Furthermore, the nanoparticles may contain a noble metal in multiple different oxidation states. In some embodiments, the noble metal ions contain a mixture of noble metal ions in both the ground state and the +1 oxidation state. In some aspects, the modification of the noble metal ion ratio may affect the emission properties such as the surface-state or the interband emission of the metal.

In certain embodiments, the nanoparticle contains a ligand capable of specifically binding to at least one cellular component or associating with a cell based upon some characteristic such as pH. In some embodiments, the targeting ligand responds to a specific pH around the surface of the cell. The cellular component may be associated with specific cell types or having elevated levels in specific cell types, such as cancer cells or cells specific to particular tissues and organs. Accordingly, the nanoparticle can target a specific cell type, and/or provides a targeted delivery for the treatment and diagnosis of a disease. The ligand permits the nanoparticle to be used to identify, detect, target, or monitor a physical state or condition, such as a disease state or condition by binding to a cognate molecule or structure. For example, a ligand may be used to detect the presence or absence of a particular receptor, expression level of a particular receptor, or metabolic levels of a particular receptor. The ligand can be, for example, a peptide, a protein, a protein fragment, a peptide hormone, a sugar (i.e., lectins), a biopolymer, a synthetic polymer, an antigen, an antibody, an antibody fragment (e.g., Fab, nanobodies), an aptamer, a virus or viral component, a receptor, a hapten, an enzyme, a hormone, a chemical compound, a pathogen, a microorganism or a component thereof, a toxin, a surface modifier, such as a surfactant to alter the surface properties or histocompatability of the nanoparticle or of an analyte when a nanoparticle associates therewith, and combinations thereof.

II. IMAGING

The present disclosure further encompasses methods of using the nanoparticles in order to study a biological state. The disclosure provides for a method of monitoring a molecule of interest by contacting the noble metal nanoparticle with a sample containing the molecule of interest. In a particular embodiment, the molecule of interest is present in a biological sample. In some embodiments, the molecule of interested is contacted in vivo.

Nanoparticle compositions of the present disclosure are capable of emitting in the near-infrared range of 500 nm to 1100 nm. Compositions of the disclosure are capable of being detected fluorescence imaging techniques. Therefore, the nanoprobes of the disclosure can serve as dual-modality imaging probes with emission modes at multiple different wavelengths.

In an embodiment of the disclosure, the compositions of the disclosure are used to monitor the pH at the surface of cell membranes. In certain embodiments of the disclosure, the cell membranes that are targeted are tumor cell membranes. In certain embodiments, the compositions of the disclosure contain a targeting moiety which causes the nanoparticle to bind or have an affinity for the surface of the cellular membrane. In certain embodiments, the nanoparticle has an affinity for the pH of the cell.

After administration of the nanoparticle to a subject, the blood residence half-life of the nanoparticles may range from about 2 hours to about 25 hours, from about 3 hours to about 20 hours, from about 3 hours to about 15 hours, from about 4 hours to about 10 hours, or from about 5 hours to about 6 hours. Longer blood residence half-life means longer circulation, which allows more nanoparticles to accumulate at the target site in vivo. Blood residence half-life may be evaluated as follows. The nanoparticles are first administered to a subject (e.g., a mouse, a miniswine or a human). At various time points post-administration, blood samples are taken to measure nanoparticle concentrations through suitable methods. In certain embodiments, suitable methods include atomic absorption spectroscopy or inductively coupled plasma mass spectrometry to determine the concentration of the noble metal in the blood.

An embodiment of the disclosure is directed to a metal nanoparticle that is renal clearable. In certain embodiments of the disclosure, the compositions demonstrate greater than 50% renal clearance within 48 hours of administration. In certain embodiments, the compositions demonstrate greater than 50% renal clearance within 24 hours of administration.

An embodiment of the disclosure is directed to a method for detecting a component of a cell comprising the steps of: contacting the cell with a composition comprising a coated noble metal nanoparticle and wherein the noble metal nanoparticle is about 0.1 nm to 5 nm in diameter; and monitoring the binding of the nanoparticle to the cell or a cellular component by two or more fluorescence imaging technique or at two or more distinct wavelengths. In some embodiments, the method comprises two or more distinct wavelength.

In some aspects, the disclosure measures the ratio of two or more distinct wavelengths from the nanoparticle composition. The ratio of these two wavelengths may be used to measure the pH of the environment that the nanoparticle composition is present in. Such pH of the environment is lower than standard physiological such that the pH may be from about pH 6 to about pH 7.4. In some embodiments, the environmental pH may be from about pH 6, 6.1, 6.2, 6.3, 6.4, 6.5, 6.6, 6.7, 6.8, 6.9, 7.0, 7.1, 7.2, 7.3, to about 7.4 or any range derivable thereof.

In some embodiments, a large number of dual-emissive nanoparticles with different surface chemistry are envisioned. Using different spectroscopic techniques such as IR absorption, fluorescence, UV-Vis absorption, XPS, TEM and DLS, the particle size, valence states, emission and the ratio of surface ligands on the NPs can be measured. Also measured are the zeta potentials of each luminescent nanoparticles as well as hydrophobicity at different pH values ranging from 7.4 to 5.3. In some embodiments, by comparing differences in zeta potentials of different types of luminescent nanoparticles, a fundamental understanding of how a protonated ligand and its hydrophobicity influence the zeta potentials can be gained. In some particular embodiments, the adsorption of serum proteins onto the luminescent nanoparticles and how the pH influences such interactions in a native biological environment can then be explored. In some embodiments, HeLa cells are used as a model system for pH-dependent membrane adsorption studies (Reshetnyak, 2006), and a fluorescence microplate reader to investigate the membrane adsorption of the NPs in the pH range of 7.4 to 5.3. In some embodiments, some nanoparticles may undergo endocytosis. In some embodiments, the studies may result in the determination of a pH threshold for the membrane adsorption of different luminescent nanoparticles.

III. THERAPY

In an embodiment of the disclosure, a therapeutic agent is attached to the nanoparticle of the present disclosure. The therapeutic agent an agent capable of treating a disease state or disorder, and may be selected from the group consisting of antibiotics, antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, extracellular matrix components, vasodialators, thrombolytics, antimetabolites, growth factor agonists, antimitotics, statins, steroids, steroidal and nonsteroidal anti-inflammatory agents, angiotensin converting enzyme (ACE) inhibitors, free radical scavengers, PPAR-gamma agonists, small interfering RNAs (siRNAs), microRNAs, and anti-cancer chemotherapeutic agents.

A further embodiment of the disclosure is directed to a method for targeting a tumor cell comprising administering to the subject an effective amount of a composition comprising a noble metal nanoparticle, wherein the surface of the noble metal nanoparticle is coated with a mercapto containing compound or amino acid derivative, and wherein the noble metal nanoparticle is about 2 nm to 10 nm in diameter.

IV. NANOPARTICLES COMPOSITIONS

A. Preparing Nanoparticles

The present disclosure further encompasses methods for the preparation of the noble metal nanoparticle having the characteristics as described herein. In one embodiment, the method of preparing a noble metal nanoparticle comprises the steps of: a) combining an aqueous solution comprising a noble metal, and an aqueous solvent to create a combined solution; b) adding a first ligand; c) mixing the combined solution to allow the formation of a noble metal nanoparticle; and d) adjusting the pH of the combined solution using acid or base.

In certain embodiments of these methods, a reducing agent is added to the combined solution to reduce the noble metal nanoparticle. In particular, the reducing agent is selected from the group comprising a chemical reducing agent, light, or a combination thereof. In certain embodiments of these methods, light can be used as a reducing agent to photoreduce the noble metal nanoparticles. In certain other embodiments of these methods, a chemical reducing agent can be used as a reducing agent. In one embodiment, light is used in combination with a reducing agent to photoreduce the noble metal nanoparticles. In some embodiments, the mercapto containing compound can act as a reducing agent. In particular embodiments, the amount of reduced noble metal atoms in the nanoparticle impacts the fluorescence emission of the compound. In some embodiments, varying the amount of reducing agent added, the identify of the reducing agent, the temperature of the reaction, or the reaction time alters the ratio of reduced noble metal atoms to charged noble metal atoms in the nanoparticle. In some embodiments, altering the ratio changes the only the interband emission, only the surface-state emission, or both types of emission. In some embodiments, increasing the ratio of reduced metal atoms to oxidized metal atoms in the nanoparticle increases the emission wavelength of one or both of the interband and surface-state emission at a given wavelength. In other embodiments, decreasing the ratio of reduced metal atoms to oxidized metal atoms in the nanoparticle increases the emission wavelength of one or both of the interband and surface-state emission at a given wavelength. In some embodiments, the ratio of reduced metal atoms to oxidized metal atoms is from about 1.0 to about 1.6.

In particular, the aqueous solution comprising a noble metal ion used in the preparation of the compounds is selected from the group consisting of $AgNO_3$, $HAuCl_4.nH_2O$, and $CuCl_2.nH_2O$. In one embodiment, the aqueous solution comprising a noble metal is $AgNO_3$. In another embodiment, the aqueous solution comprising a noble metal is $HAuCl_4.nH_2O$. In a further embodiment, the aqueous solution comprising a noble metal is $CuCl_2.nH_2O$.

In one embodiment, the aqueous solution comprising a noble metal is $HAuCl_4.nH_2O$, a reducing agent is added to the combined solution along with a ligand, the pH adjusted, and the combined solution is mixed for at least one hour to allow the formation of the gold nanoparticle. In another embodiment, the pH adjusted, combined solution is mixed for about 48 hours or longer (up to several months) to allow the formation of a luminescent gold nanoparticle. In another embodiment, noble metal nanoparticles are created through photoreduction through irradiation with visible or ultraviolet light to allow the formation of a gold, silver or copper nanoparticle. In this work, the inventors used the weak reducing property of thiolated ligands to reduce gold ions in the gold nanoparticles.

In some embodiments, to synthesize these dual emissive AuNPs with pH dependent membrane adsorption, gold ions are mixed with a thiol containing ligand (or mixture of ligands) such as glutathione, 2-mercaptoethanol, cysteamine, or N-acetyl-L-cysteine at the certain ratio such as 2:1, 1:1, 1:2. In some specific embodiments, the ratio between glutathione and cysteamine ligand can also be tuned from 1:1 to 1:0.75, 1:0.5, 1:0.25, 1:1.5, 1:2, 1:2.5, 1:3.

Figure 14:
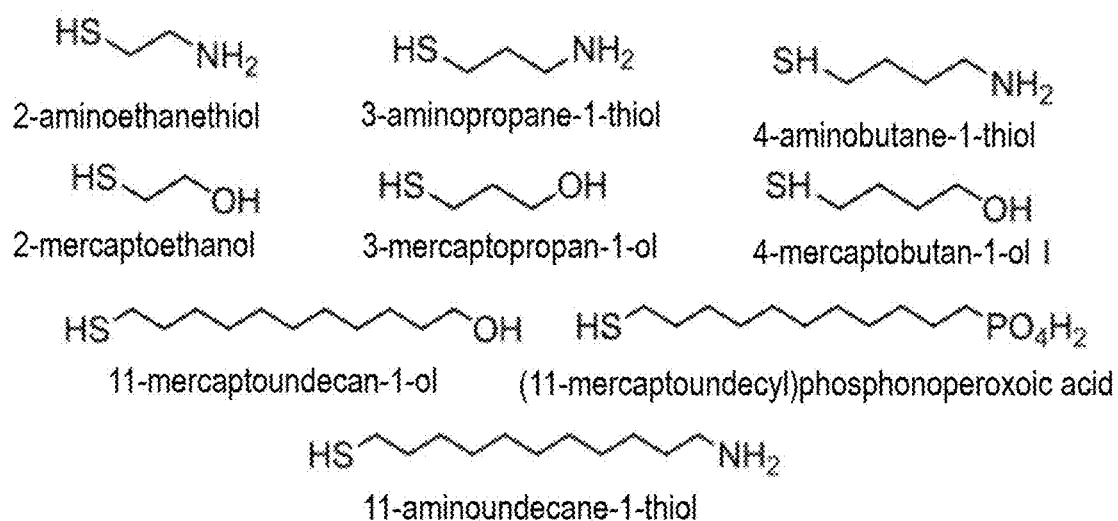
FIG. 14 shows a non-limiting set of examples of thiolated ligands that can be used for enhancing the hydrophobicity of luminescent AuNPs.

In some embodiments, the amphiphilic nature of the cell membrane also provides another route for membrane targeting. The previous studies have shown that hydrophobic ligand can minimize serum protein adsorption to negatively charged AuNPs and assist them to cross the cell membrane (Verma, et al., 2008). Since hydrophobic interactions is also long range like electrostatic interactions but decay exponentially with distance (Israelachvili and Pashley, 1982), the driving force for the NPs bound to the cell membrane will be hydrophobic interactions once the NPs become very close to the cell membrane. In some embodiments, to increase the hydrophobic interactions between GS-AuNPs and the cell membrane, thiolated hydrophobic ligands are incorporated, in addition to glutathione and cysteamine ligands, into the luminescent AuNPs. FIG. 14 contains a non-limiting set of examples of the types of ligands with different hydrophobicity which can be incorporated into the nanoparticles. The hydrophobicity of these ligands is measured based on their partition in oil and water. These ligands are commercially available and will be used to create the luminescent AuNPs together with glutathione. In some preferred embodiments, the ratio between Au ions and S, and the ratio between glutathione and a thiolated hydrophobic ligand with different hydrophobicity and surface charge is tuned. Since GC-AuNPs have already exhibited pH dependent, without being bound by theory, introducing additional hydrophobic ligands with primary amine groups such as aminopropane thiol and aminobutane thiol are expected to further enhance the binding affinity of the NPs to the cell membrane in mild acidic extracellular environment.

B. Pharmaceutical Compositions

In some aspects, the nanoparticles of the present disclosure will be formulated as pharmaceutical composition, i.e., suitable for administration to patients. Pharmaceutical compositions of the present disclosure comprise an effective amount of a nanoparticle dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present disclosure can be administered intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present disclosure. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in particular embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the disclosure, the oral composition may be prepared as a syrup or elixir. A syrup or elixir, and may comprise, for example, at least one active agent, a sweetening agent, a preservative, a flavoring agent, a dye, a preservative, or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula includes

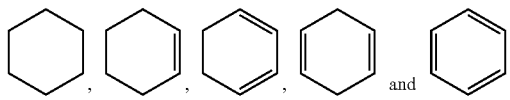

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "〜〜", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂━" means a single bond where the group attached to the thick end of the wedge is "out of the page." The symbol "▪▪▪▪▪" means a single bond where the group attached to the thick end of the wedge is "into the page". The symbol "〜〜" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

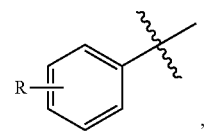

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

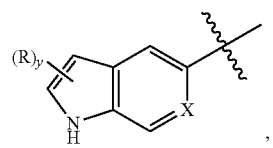

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkanes/alkenyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

An "amino acid" is a functional group which contains a —CO$_2$H and a —NH$_2$ group on the same carbon skeleton. In some embodiments, the term "amino acids" refer to a functional group in which both the —CO$_2$H and the —NH$_2$ are attached to the same carbon atom; which may also be known as an "α-amino acid". In its preferred embodiment, the term "amino acid" refers to one of the naturally occurring or commercially available amino acids as well as their enantiomers and diastereomers. In its most preferred embodiment, the term "amino acids" refers the 20 canonical amino acids, a protected version of one of the 20 canonical amino acids, and their enantiomers and diastereomers. As used herein, the term "amino acid residue" refers to a divalent amino acid which is linked through both the amine group and carboxylate group as shown, e.g.,

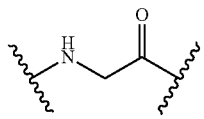

As used herein, the term "noble metal" refers to the group of elements selected from the group consisting of gold, silver, and copper and the platinum group metals (PGM) platinum, palladium, osmium, iridium, ruthenium and rhodium. In certain particular embodiments of the present disclosure, the noble metal is selected from the group consisting of gold, silver, and copper. In some particular embodiments, the noble metal is gold or silver.

As used herein, the term "nanoparticle" refers to an association of 2-1000 atoms of a metal. Nanoparticles may have diameters in the range of about 2 to about 5 nm. In other particular embodiments, the nanoparticles comprise approximately 2-1000, approximately 2-500, approximately 2-250, approximately 2-100, approximately 2-25 atoms, or approximately 2-10 atoms. As used herein, the terms "nanoparticle composition" references to a noble metal nanoparticle as described herein.

As used herein, the term "labeled" refers to an entity, e.g., a nanoparticle that carries a molecule capable of detection, either directly or indirectly.

As used herein, the term "hydrodynamic diameter" refers to the diameter of the particles in the solution, which includes the actual size and hydrodynamic water layer.

As used herein, the term "nanoparticle core" refers to metal core of the particles.

As used herein, the term "about" refers to the stated value, plus or minus 5% of that stated value.

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

VI. EXAMPLES

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1

Materials and Methods

Hydrogen tetrachloroaurate used for the synthesis of the luminescent glutathione coated AuNPs was obtained from Fisher Scientific (U.S.). All the other chemicals were obtained from Sigma-Aldrich and used as received unless specified.

The pH responsive dual emissive AuNPs were synthesized by thermally reducing $HAuCl_4$ with glutathione in the presence of Tris(2-carboxyethyl)phosphine hydrochloride (TCEP) ligands in aqueous solution. In a typical synthesis, 5 mL 24 mM glutathione was adjusted to pH 7~8 with 1 M NaOH, followed by adding 135 μL 0.3 M TCEP to the solution ($C_{TCEP}/C_{glutathione}=1/3$), and incubated for 30 min, followed by transferring the mixture to a three-necked bottle with 45 mL DI $H_2O$. The mixture was then added 150 μL 1 M $HAuCl_4$ and heated in oil-bath at 95° C. under continuously stirring. The color of the solution changed from light yellow to light brown, indicating the formation of the GS-AuNPs. The reaction took about 45 min to complete as confirmed by the maximum of the time dependent fluorescence intensity of the solution monitored by a fluorescence spectrometer. The resulting solution was cooled down to room temperature and purified by an ethanol precipitation method, and then further purified with NAP-5 column to remove all the free glutathione ligands and large aggregates.

Figure 15:
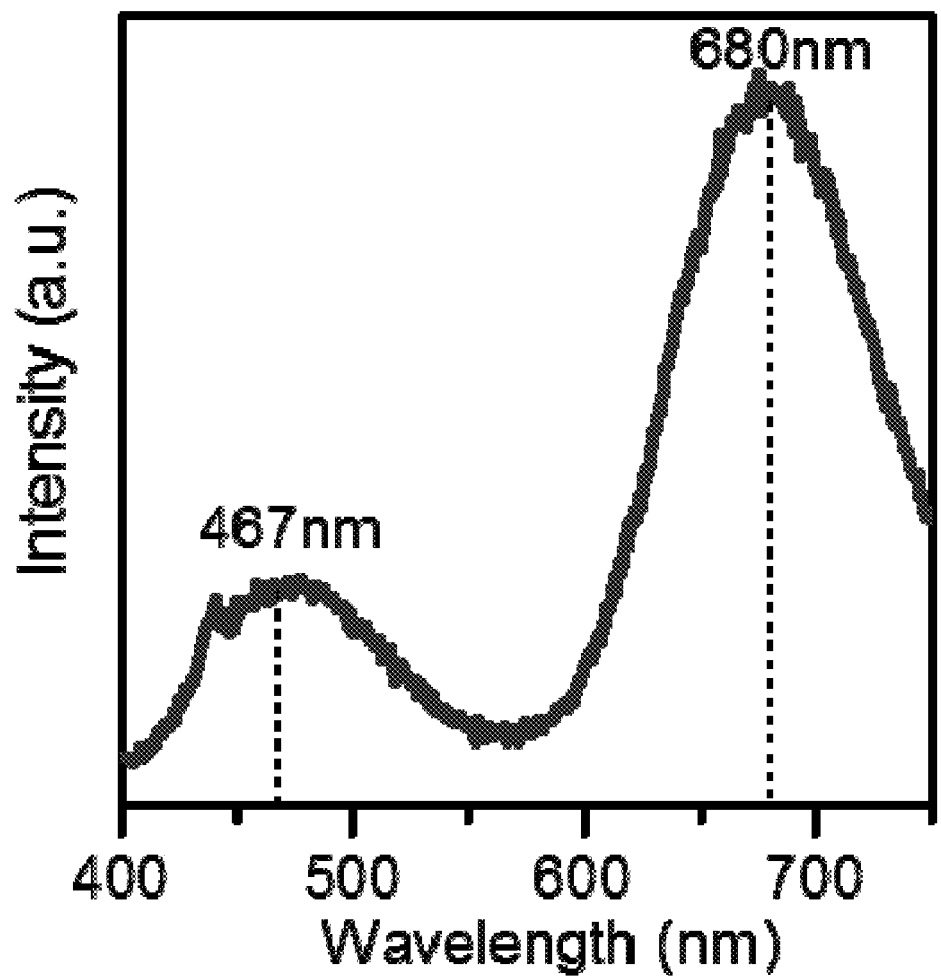
FIG. 15 shows the fluorescence spectrum of Ag-GSH NPs.

In the synthesis to produce Ag-GSH nanoparticles, freshly prepared aqueous solutions of $AgNO_3$ (1M, 0.05 mL) and GSH (L-GSH; 0.4M, 0.3 mL) were mixed with 40 mL of DI water with gentle stirring at room temperature. Subsequently, 1 M NaOH were added to the solution with vigorous stirring to adjust pH of solution to ~5. Finally, the solution was stirred and incubated at 95° C. for several hours to produce dual emissive Ag-GSH coated NPs. The emission spectrum of the Ag-GSH nanoparticle is shown in FIG. 15.

Example 2

Design and Synthesis of Dual Emission pH Responsive Nanoparticles

A. Luminescent GS-AuNPs with Interband Emission (iGS-AuNPs)

By taking advantage of reducing property of glutathione and unique dissociation process of glutathione(GS)-gold(I) polymers (Zhou, et al., 2006), the inventors were able to create 1.7 nm orange emitting AuNPs (OGS-AuNPs) with a maximum at 565 nm (FIGS. 1A-B) and 2.1 nm yellow emitting AuNPs (YGS-AuNPs) with a emission maximum at 545 nm (FIGS. 1C-D). Quantum yields of these few-nm GS-AuNPs were measured to be $4.0 (\pm 0.4) \times 10^{-2}$, which is one or two-order higher than many previously known luminescent gold nanoclusters. The emission lifetime of iGSAuNPs at 530 nm excitation, a wavelength close to interband (sp-d) gap, is around 2.8 ns, indicating that the observed luminescence fundamentally arises from the combination of electrons in the sp band and the holes in the d bands. X-ray photoelectron spectroscopic (XPS) studies on Au 4f2/7 binding energy (BE) of these iGS-AuNPs show that nearly 49% and 45% of Au atoms in the OGS-AuNPs and yellow emitting AuNPs (YGSAuNPs) are in the Au(I) oxidation state respectively, which are significantly different from the same sized nonluminescent GS-AuNPs. The similar valence-state effect was also observed from many other few-nm thiolated luminescent AuNPs. For example, Huang et al. used several alkanethiol ligands such as 2-mercaptoethanol, 6-mercaptohexanol, and 11-mercaptoundecanol to stabilize 2.9 nm luminescent AuNPs with emission ranging from 500 nm to 618 nm (Huang, et al., 2007). Guo et al. later used 11-mercaptodundecanoic acid as a protecting group to stabilize 2.7 nm luminescent AuNPs with emission at 615 nm (Guo, et al., 2012). The common feature for this class of luminescent AuNPs is that a large amount of Au(I) atoms exist in the NPs, further indicating importance of Au valence states in the enhancing quantum efficiencies of interband emission from AuNPs.

B. GS-AuNPs with Surface-State Emission (sGS-AuNPs)

In addition to interband transition, surface-state emission is another important photophysical mechanism that can make few nm AuNPs highly luminescent. Unlike interband emission that is usually in the range of about 500 to about 680 nm, surface states generally emit at even longer wavelength (about 700 nm to about 1100 nm) (Wang, et al., 2005). Glutathione can also serve as an excellent capping ligand for creating luminescent AuNPs with NIR emission. Shown in FIG. 2 is 2.5 nm GS-AuNPs that can emit 810 nm with quantum efficiency of 0.8% (Zhou, et al., 2012). Photoluminescence lifetime studies indicate that emission lifetime is around 4 μs, further indicating that surface-state emission follows a photophysical mechanism different from the interband emission. The observed NIR emission fundamentally arises from hybrid electronic states formed by surface gold atoms and thiolated ligands. Because NIR emission originates from surface states, it varies very modestly with particle size and valence states. For example, all the fully reduced Au13, Au38, and Au140 give emission in the range of 885 to 1100 nm (Wang, et al., 2006). On the other hand, because the emission is involved with hybrid electronic states of surface gold atoms and thiolated ligands, the interactions between the thiolated ligands and surface gold atoms become critical to emission wavelengths. Indeed, Wang et al. found that polarity of thiolated ligands significantly influences quantum efficiencies of IR-emitting AuNPs (Wang, et al., 2006).

C. pH Responses of Luminescent GS-AuNPs with Different Emission Mechanisms

Since the emission of luminescent AuNPs can originate from two different mechanisms, a natural question is whether these two different types of emissions response to pH changes differently. Shown in FIG. 3A is the emission intensities of NIR emitting GS-AuNPs in the different pH values ranging from 5 to 10, which monotonically increases once pH is lowered. However, iGS-AuNPs with 600 nm emission exhibit an opposing pH-dependence: with the decrease of pH from 10 to 5, the emission intensity is decreased nearly 50% (FIG. 3B). Since both luminescent AuNPs are coated with the same glutathione ligand, the protonation of glutathione in these two different types of GS-AuNPs will be the same. Because glutathione has four different $pK_a$ values (2.12, 3.53, 8.66, and 9.62, respectively) (Brinas, et al., 2008); in the pH range from 4 to 8, protonation of amine group of glutathione is likely responsible for the observed pH-dependent emission. Without being bound by theory, the pH response of iGS-AuNPs is similar to that of QDs. Based on the previous studies of pH responsive QDs (Liu, et al., 2007), the protonation of thiolated ligands on the surface of QDs will weaken the interactions between the ligands and QDs and impair ligand passivation, resulting in the decrease of quantum efficiencies of QDs. This proposed quenching mechanism might also work for iGS-AuNPs because the interband emission from iGS-AuNPs is similar to bandgap emission from QDs and very sensitive to ligand passivation. In contrast, protonation of glutathione ligand resulted in the opposite pH response of surface-state emission from sGS-AuNPs, which might be because weakening gold-thiolated ligand interactions and impaired passivation result in the formation of more surface states. It should be noted that pH-dependent surface-state and interband emissions from GS-AuNPs are reversible (FIGS. 3C-D), suggesting that the protonation of thiolated ligands does not result in the complete desorption of GS ligand from the surface of luminescent AuNPs. Since protonation of GS ligand results in the opposite responses from different types of emissions of luminescent GS-AuNPs, a new class of fluorescent ratiometric pH indicators can be created if these two emission centers can be simultaneously incorporated in the one single AuNP.

D. Dual Emissive Glutathione Coated Gold Nanoparticles

Since two different types of emissions have been observed from ~2-3 nm GS-AuNPs, the efforts to prepare and optimized dual-emissive GS-AuNPs have been carried out. Previous studies on photophysical mechanisms of luminescent GS-AuNPs have shown that interband emission is dependent on the ratio of Au(I) and Au(0) in the particles but surface-state emission is only dependent on the interactions between the thiolated ligands and surface Au atoms. Therefore, it is feasible to adjust Au(I)/Au(0) ratios of GS-AuNPs to achieve dual-emissive GS-AuNPs. A very small amount of reducing agents were added during the synthesis of iGS-AuNPs, and found that a new emission band at 800 nm started emerging (FIG. 4A). To confirm that dual emission bands originated from the same NPs, the inventors further used gel electrophoresis, a tool that has been widely used to purify ligand capped AuNPs, to purify dual-emissive AuNPs. These results indicated that dual emission bands indeed originated from a single component (FIG. 4B). Coexistence of the two emissions in one particle suggested that energy transfer between them is not efficient, which might be due to the lifetime of 800 nm emission is much longer than that of 600 nm one. Studies on the pH responses of these dual emissive GS-AuNPs (600/800) were also carried out. The results of these studies are shown in FIG. 5A are luminescence spectra of 600/800 dual emissive AuNPs obtained at different pH values. With the decrease of pH from 10 to 4.5, the intensity of 800 nm emission dramatically increased along with the decrease of 600 nm emission intensity. The intensity ratio of the 800 nm emission to the 600 nm emission exhibits more than 6-fold differences within a physiological pH range from 7.4 to 5 and the pH threshold for the observed pH-dependent emission is around 6.95 (FIG. 5B). The ratiometric response is also reversible, indicating that these dual-emissive AuNPs indeed can serve as fluorescent indicators for quantitative pH imaging within a physiological pH range. Based on these results, further studies on how the ratio of Au(I)/Au(0) quantitatively influences surface-state and interband emission of AuNPs. Without being bound by theory, the Au(I)/Au(0) ratio can be tuned by introducing different amounts of reducing agents and changing heating temperatures as well as reaction time. XPS studies can be used to quantify the ratio of Au(I)/Au(0).

E. Tuning Emission Wavelength

For in vivo application, ideally, both emission wavelengths would fall into the deep red and NIR range. Since ligand polarity, charges and its capability of donating electrons have significant influences on the interactions between surface gold atoms and ligands, surface ligands will be used to tune emission wavelength of surface states into NIR range. Galvanic ligand exchange methods can be used to achieve this goal (Huang and Murray, 2003). Previous studies have shown that after coating AuNPs with 2-mercaptoethanol, 3-mercaptopropionic acid, N-acetyl-L-cysteine and (2-mercaptopropionyl)glycine, surface states of these thiolated ligand capped AuNPs can give even longer emission from about 920 to about 1100 nm (Wang, et al., 2006). Inspired by those studies, these ligands are used to partially displace glutathione and tune surface state emission of GS-AuNPs. Alternatively, NIR emitting AuNPs coated with 2-mercaptoethanol, 3-mercaptopropionic acid, N-acetyl-L-cysteine and (2-mercaptopropionyl)glycine can be synthesized separately and then glutathione used to partially replace those ligands. Using the modification of the surface ligands, the surface-state emissions are turned.

Example 3

Biologic Studies of Glutathione Coated Nanoparticles

A. Glutathione Coated Nanoparticles have High Resistance to Serum Protein Absorbance and Effective Renal Clearance Studies show that very little changes in the HDs before and after fetal bovine serum (FBS: 6 nm) incubation, indicating that GS-AuNPs have little interactions with serum proteins (FIG. 6A), also confirmed by gel electrophoresis studies. Biodistribution of these luminescent GS-AuNPs in vital organs was characterized at 24-hour p.i. In sharp contrast to previously reported biodistribution of 1.4 nm, 5 nm and 18 nm AuNPs, which showed about 50% to about 94% of the NPs in the liver (Semmler-Behnke, et al., 2008; Lipka, et al., 2010), more than 55% of the particles were excreted into the urine and only 3.7±1.9% of GS-AuNPs were accumulated in the liver, and 8.8±2.0%, 4.4±2.1% and 0.3±0.1% of the particles were found in the kidney, lung and spleen, respectively (FIG. 6B) (Zhou, et al., 2011). These studies suggested that glutathione is a promising ligand to minimize nonspecific adsorption of serum proteins and enhance renal clearance efficiency of NPs.

B. Photostability of 800 nm Emitting GS-AuNPs in the Presence of Serum Proteins

Success of the nanoparticles is also strongly dependent on photostability and brightness of luminescent AuNPs in native physiological environment; therefore, studies were conducted to test the feasibility of using luminescent AuNPs for in vivo tumor imaging (FIGS. 7A-B). Luminescent AuNPs with 800 nm emission and a quantum efficiency of 0.8% were used as a model system for the studies to investigate in vitro physiological stabilities of the NPs in the presence of serum proteins at 37° C. Interestingly, fluorescence intensities of the NPs in phosphate buffered saline (PBS) containing 10% (v/v) fetal bovine serum (FBS) were slightly increased by 5% compared to those in PBS solution without FBS. After 24 h incubation with FBS, little change was observed in fluorescence intensity, indicating that GS-NPs are stable in physiological environment.

C. Tumor Targeting of 800 nm Emitting Gold Nanoparticles

After coated glutathione, luminescent AuNPs behave like small molecules in renal clearance, but whether such small GS-AuNPs still can target the tumor through well-known enhanced permeability and retention (EPR) effect (Matsumura and Maeda, 1986) as large NPs do is an unknown question. The tumor targeting kinetics of 800 nm emitting GS-AuNPs in both normal and tumor tissues were studied. Due to the differences in vascular structure or metabolism between tumor and normal tissues (Danhier, et al., 2010), GS-AuNPs show preferred accumulation in the tumor (FIG. 8A). Retention kinetics of the particles in normal tissue showed two-compartment decay (FIG. 8B): more than 90% of the particles were eliminated from the normal tissues with a half-life of 43.4±6.6 min and less than ~10% of the particles remained in the normal tissue for more than 24 h (FIG. 8B), indicating that these NPs have high biocompatibility. The NPs reached their maximum accumulation at the tumor sites within 40 min and nearly 90% of the particles remained in the tumor after 24 h of p.i. (FIG. 8C), implying that luminescent GS-AuNPs indeed can target tumor and retain long time in the tumor through EPR effect even though they are extremely small. Since GS-AuNPs are highly resistant to serum protein adsorption and highly negatively charged, no significant binding to the cell membrane or internalization by the cells in the presence of serum proteins like large NPs generally do was observed. The accumulation of 600 nm emitting AuNPs in the bladder (FIG. 9) was observed therefore, no problem observing the 600 nm emission from the tumor is expected as well.

Example 4

Figure 11:
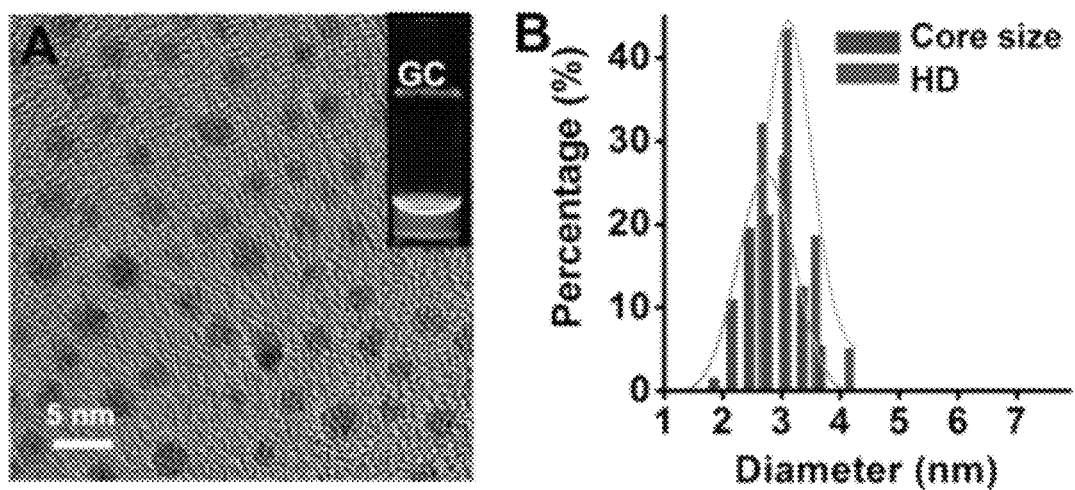
FIGS. 11A-B show glutathione and cysteamine coated luminescent AuNPs (GC-AuNPs).
Figure 12:
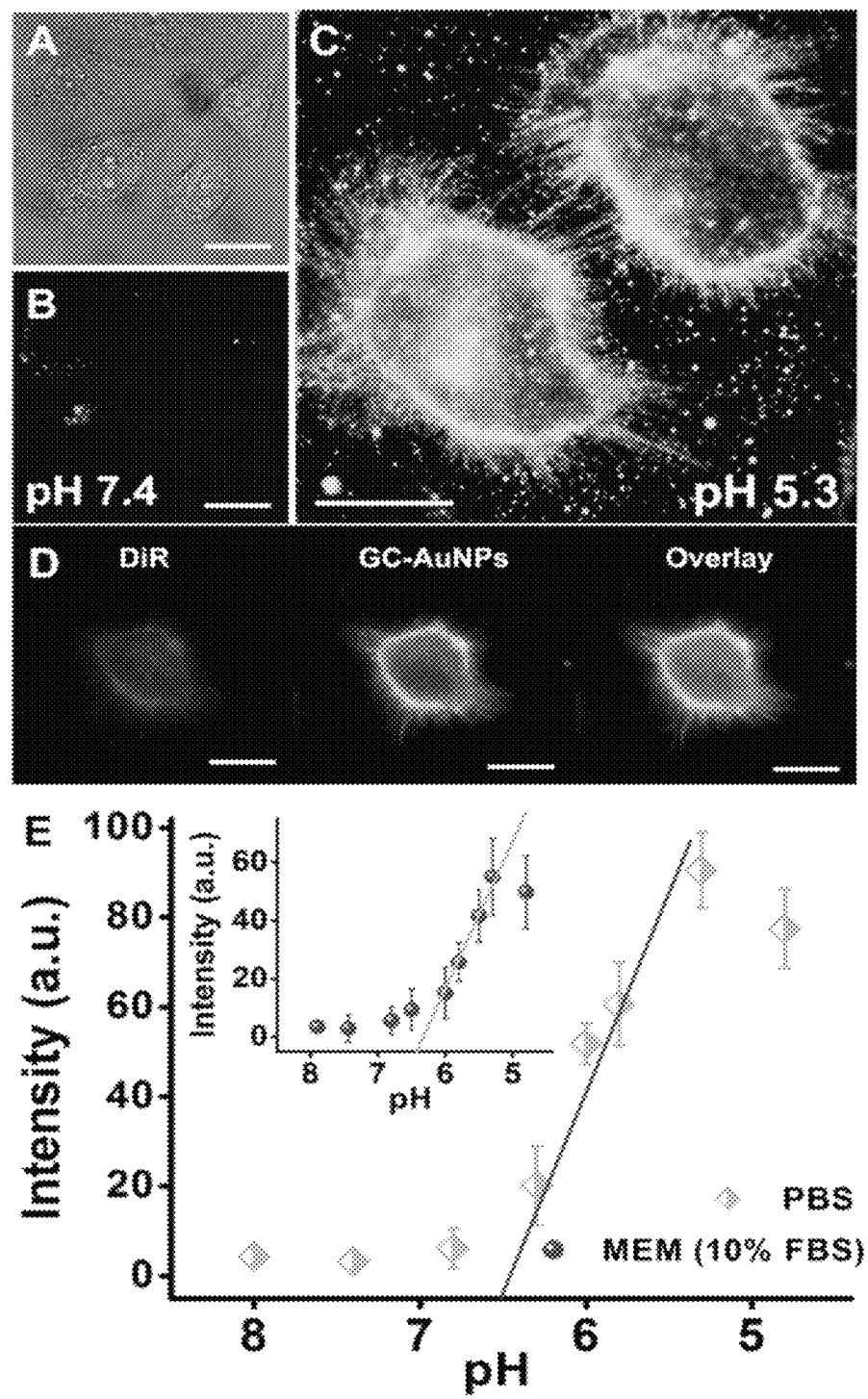
FIGS. 12A-12E show pH-dependent adsorption of GC-AuNPs on live cell membrane. Brightfield (FIG. 12A) and fluorescence (FIGS. 12B-12D) images of live HeLa cells incubated with 0.2 mg/mL GC-AuNPs at pH 7.4 (FIGS. 12A-B) and 5.3 (FIG. 12C) in PBS at 25° C. for 10 min (FIGS. 12A-12C, 12E: scale bar, 20 μm).

Gold Nanoparticles with pH-Dependent Ratiometric Emission and Membrane Adsorption A. Gold Nanoparticles with pH-Dependent Membrane Adsorption The earlier examples have shown that serum proteins were not adsorbed onto GS-AuNPs, and no any adsorption of GS-AuNPs to the cell membrane was observed either in a pH range from 7.4 to 5.3. This observation is rooted in the fact that GS-AuNPs are highly negatively charged (zeta potential: −35.54±2.77 mV at pH 5.3) in weakly acidic condition. Since small AuNPs coated with cysteamine (CA) are positively charged (zeta potentials: +31.24±2.41 mV and +13.95±2.75 mV at pH 5.3 and pH 6 respectively) and can be nonspecifically absorbed onto the cell membrane, CA was incorporated into the nanoparticle as the secondary ligand into GS-AuNPs and obtained luminescent AuNPs coated by both glutathione and cysteamine (GC-AuNPs), which showed interesting pH-dependent membrane adsorption. The luminescent GC-AuNPs with particle size of 2.7 nm and HD of 3.1 nm are shown in FIG. 11. The membrane adsorption of GS-AuNPs and GC-AuNPs at different extracellular pH was investigated, and found that the introduction of protonated CA indeed rendered luminescent AuNPs with pH-dependent membrane adsorption (FIGS. 12A-E). At pH 7.4, GS-AuNPs and GC-AuNPs have little interactions with the cell membrane but GC-AuNPs strongly bound to the cell membrane at pH 5.3. As shown in FIG. 12C, even the plasma membrane of filopodia was well imagined using GC-AuNPs. Colocalization of a membrane dye and GC-AuNPs (FIG. 12D) indicated that GC-AuNPs were indeed absorbed onto the cell membrane. Further quantitative studies showed that the pH threshold for the membrane adsorption of GC-AuNPs is about 6.5 in both PBS and cell medium (FIG. 12E), indicating that serum proteins have little effects on the binding of the NPs to the cell membrane.

B. Targeting Efficiency of Gold Nanoparticles

Figure 13:
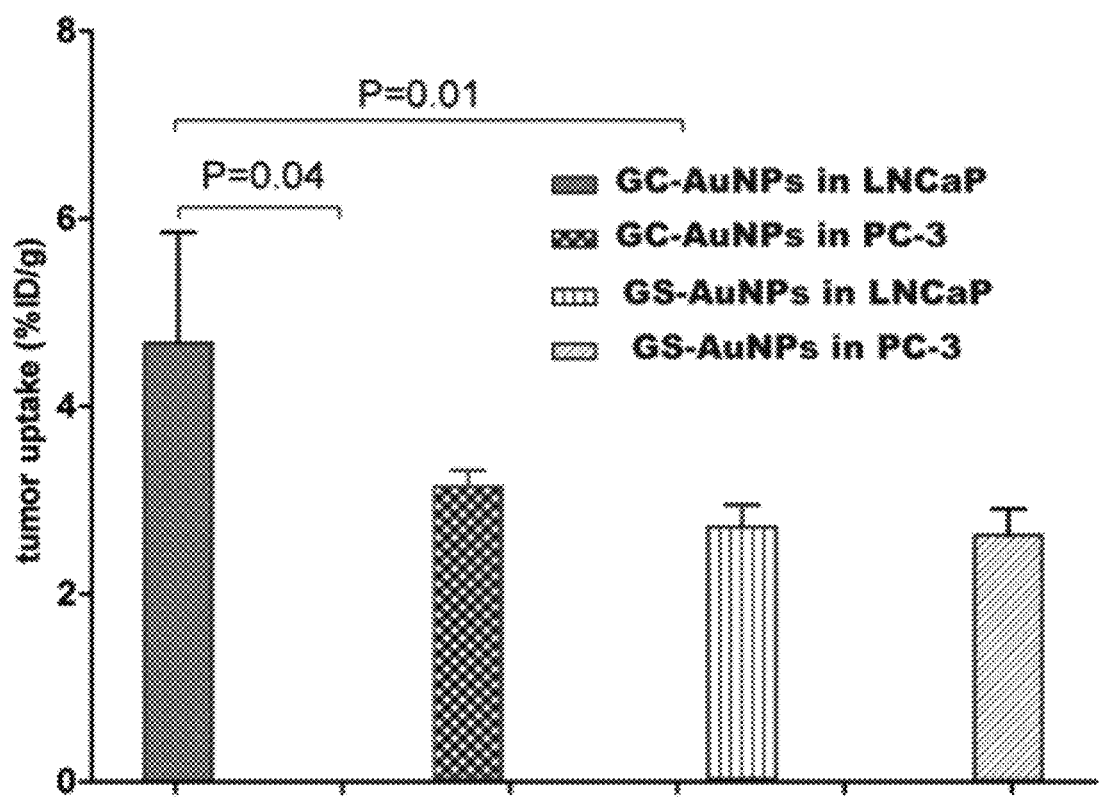
FIG. 13 shows tumor uptake of GS-AuNPs with no pH-dependent membrane adsorption and GC-AuNPs with pH dependent membrane adsorption in LNCaP and PC-3 tumors.

The preliminary tumor biodistribution of GC-AuNPs (pH-dependent membrane adsorption) and GS-AuNPs (no pH-dependent membrane adsorption) in LNCaP and PC-3 tumor bearing mice (FIG. 13) were analyzed to test whether introducing additional CA ligand into GS-AuNPs can enhance targeting specificity to acidic tumors. While the pH-dependent membrane adsorption of GC-AuNPs has yet to be optimized, its accumulation is 50% higher than that of GS-AuNPs (pH non-sensitive) in LNCaP tumors and 75% more than that in PC-3 tumor. These results clearly demonstrate that tuning surface chemistry of luminescent AuNPs can enhance the targeting effectiveness for the acidic microenvironment.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference:

Ardeshirpour, et al, *Technology in Cancer Research & Treatment*, 10:549-560, 2011.
Bizzarri, et al., *Analytical and Bioanalytical Chemistry*, 393:1107-1122, 2009.
Briggs, et al., *Chemical Communications*, 2323-2324, 2000.
Brinas, et al., *Journal of the American Chemical Society*, 130:975-982, 2008.
Brown, *Cancer Biology & Therapy*, 1:453-458, 2002.
Canton and Battaglia, *Chemical Society Reviews*, 41:2718-2739, 2012.
Casals, et al., *ACS Nano*, 4:3623-3632, 2010.
Choi, et al., *Nature Biotechnology*, 25:1165-1170, 2007.
Chudakov, et al., *Trends in Biotechnology*, 23:605-613, 2005.
Danhier, et al., *Journal of Controlled Release*, 148:135-146, 2010.
Dennis, et al., *ACS Nano* 6:2917-2924, 2012.
Gao, et al., *Journal of Biomedical Optics*, 7:532-537, 2002.
Gatenby and Gawlinski, *Cancer Research*, 56:5745-5753, 1996.
Gatenby, et al., *Cancer Research* 66:5216-5223, 2006.

Gillies, et al., *IEEE Engineering in Medicine and Biology Magazine*, 23:57-64, 2004.
Glaasker, et al., *Molecular Membrane Biology*, 13:173-181, 1996.
Guo, et al., *Analyst*, 137:301-304, 2012.
Han and Burgess, *Chemical Reviews*, 110:2709-2728, 2010.
Hashim, et al., *NMR in Biomedicine*, 24:582-591, 2011.
Hirsjarvi, et al., *Current Drug Discovery Technologies*, 8:188-196, 2011.
Huang and Murray, *Journal of Physical Chemistry B*, 107: 7434-7440, 2003.
Huang, et al., *Angewandte Chemie International Edition*, 46:6824-6828, 2007.
Israelachvili and Pashley, *Nature*, 300:341-342, 1982.
Khramtsov, *Current Organic Chemistry*, 9:909-923, 2005.
Lakadamyali, et al., *Cell*, 124:997-1009, 2006.
Lesniak, et al., *Biomaterials*, 31:9511-9518, 2010.
Lipka, et al., *Biomaterials*, 31:6574-6581, 2010.
Liu, et al., *Journal of the American Chemical Society*, 130:1274-1284, 2008.
Liu, et al., *The Journal of Physical Chemistry C, Nanomaterials and Interfaces*, 111:2872-2878, 2007.
Lundqvist, et al., *Proceedings of the National Academy of Sciences of the United States of America* 105:14265-14270, 2008.
Mansfield, *Current Pharmaceutical Biotechnology*, 11:628-638, 2010.
Matsumura and Maeda, *Cancer Research*, 46:6387-6392, 1986.
Mishra, et al., *Chemical Reviews*, 100:1973-2011, 2000.
Povrozin, et al., *Analytical Biochemistry* 390:136-140, 2009.
Reshetnyak, et al., *Proceedings of the National Academy of Sciences of the United States of America* 103:6460-6465, 2006.
Schaeferling, *Angewandte Chemie International Edition*, 51:3532-3554, 2012.
Schipper, et al., *Small*, 5:126-134, 2009.
Semmler-Behnke, et al., *Small*, 4:2108-2111, 2008.
Sevick-Muraca in Annual Review of Medicine, Vol 63, Vol. 63. (eds. C. T. Caskey, C. P. Austin & J. A. Hoxie) 217-231, 2012).
Shang, et al., *Nano Today*, 6:401-418, 2011.
Snee, et al, *Journal of the American Chemical Society* 128:13320-13321, 2006.
Urano, et al., *Nature Medicine*, 15:104-109, 2009.
Verma, et al., *Nature Materials*, 7:588-595, 2008.
Wang, et al., *Journal of Physical Chemistry B*, 110:20282-20289, 2006.
Wang, et al., *Journal of the American Chemical Society*, 127:812-813, 2005.
Zheng, et al., *Nanoscale*, 4:4073-4083, 2012.
Zheng, et al., *Physical Review Letters*, 93, 2004.
Zheng, et al., *Annual Review of Physical Chemistry*, 58:409-431, 2007.
Zhou, et al., *Nanoscale*, 4(14):4228-4233, 2012.
Zhou, et al., *Angewandte Chemie* (International Ed. in English), 51:10118-10122, 2012.
Zhou, et al., *Angewandte Chemie International Edition* 50:3168-3172, 2011.
Zhou, et al., *The Journal of Physical Chemistry C*, 114: 7727-7732, 2010.

What is claimed is:

1. A nanoparticle comprising a noble metal nanoparticle, wherein:
the noble metal nanoparticle is about 0.1 nm to about 5 nm in diameter; and
the noble metal nanoparticle comprises a mixture of metal atoms in the ground oxidation state and a charged oxidation state, wherein the ratio of ground oxidation state noble metal atoms to charged noble metal atoms is from about 1.0 to about 1.6, said nanoparticle exhibiting distinct photon emissions based on ratiometric pH responses;
wherein the distinct photon emissions comprise (a) a reversible interband emission resulting in a fluorescence emission spectra comprising a first fluorescence peak and (b) an surface-state emission resulting in a second fluorescence peak; and wherein the surface of the noble metal nanoparticle is coated with a first pH-dependent ligand.

2. The nanoparticle of claim 1, wherein the noble metal nanoparticle is a gold nanoparticle or a silver nanoparticle.

3. The nanoparticle of claim 1, wherein the charged oxidation state is the +1 oxidation state.

4. The nanoparticle of claim 1, wherein the first pH-dependent ligand is 2-mercaptoethanol, cysteamine, 3-mercaptopropionic acid, N-acetyl-L-cysteine, (2-mercaptopropionyl)glycine, or glutathione.

5. The nanoparticle of claim 1, wherein the coating further comprises a second pH-dependent ligand.

6. The nanoparticle of claim 5, wherein the ratio of the first and second pH-dependent ligand to the metal atoms in the noble metal nanoparticle is from about 3:1 to about 1:3.

7. The nanoparticle of claim 1, wherein the noble metal nanoparticle is about 1.5 nm to about 3 nm in diameter.

8. The nanoparticle of claim 1, wherein the first fluorescence peak is centered from about 500 nm to about 1200 nm and the second fluorescence peak is centered from about 750 nm to about 1200 nm.

9. The nanoparticle of claim 1, wherein a ratio of the peak area from the first to the second fluorescence peak changes as the pH of the environment changes.

10. The nanoparticle of claim 1, wherein the noble metal nanoparticle further comprises a targeting ligand.

11. A method of using the nanoparticle of claim 1 to image a tumor comprising:
contacting the noble metal nanoparticle with the extracellular matrix around the tumor;
exposing the nanoparticle to an excitation source; and
obtaining a fluorescence reading from a first and second fluorescence emission wavelength selected from a reversible interband and surface-state fluorescence emission of the nanoparticle.

12. The method of claim 11, wherein the excitation source produces light of a wavelength from about 450 nm to about 600 nm or about 600 nm to about 800 nm.

13. The method of claim 11, wherein the first fluorescence emission wavelength is from about 500 nm to about 750 nm and the second fluorescence emission wavelength is from about 750 nm to about 1200 nm.

14. The method of claim 11, wherein the extracellular matrix further comprises an extracellular pH ($pH_e$) which is different from the pH of normal tissue.

15. The method of claim 14, wherein the $pH_e$ is from about 6 to about 7.4.

16. The method of claim 11, wherein the noble metal nanoparticle is a gold nanoparticle or a silver nanoparticle.

17. The method of claim 11, further comprising measuring the emission of the noble metal nanoparticles at 600 and 800 nm and calculating the ratio of the emission at 800 nm around the tumor to the emission at 600 nm around the tumor.

18. The method of claim 11, wherein the pH dependent ligand coating on the noble metal nanoparticle further comprises a first and a second pH dependent ligand.

19. The method of claim 11, wherein the tumor is imaged in vivo.

20. A method of imaging a change in a patient's extracellular physiological pH in vivo comprising administering to the patient the nanoparticle of claim 1, and performing diagnostic imaging.

* * * * *